(12) United States Patent
Lee et al.

(10) Patent No.: US 10,559,101 B2
(45) Date of Patent: Feb. 11, 2020

(54) METHOD AND APPARATUS FOR GENERATING X-RAY TOMOGRAPHIC IMAGE DATA

(71) Applicants: Samsung Electronics Co., Ltd., Suwon-si, Gyeonggi-do (KR); Korea Advanced Institute Of Science And Technology, Daejeon (KR)

(72) Inventors: Jong Ha Lee, Suwon-si (KR); Ho Yeon Lee, Daejeon (KR); Seung Ryong Cho, Daejeon (KR)

(73) Assignees: SAMSUNG ELECTRONICS CO., LTD., Suwon-si (KR); KOREAN ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/181,685

(22) Filed: Nov. 6, 2018

(65) Prior Publication Data
US 2019/0139276 A1 May 9, 2019

(30) Foreign Application Priority Data
Nov. 6, 2017 (KR) .................. 10-2017-0146945

(51) Int. Cl.
*G06T 11/00* (2006.01)
*A61B 6/02* (2006.01)

(52) U.S. Cl.
CPC ............ *G06T 11/008* (2013.01); *A61B 6/025* (2013.01); *G06T 11/005* (2013.01);
(Continued)

(58) Field of Classification Search
CPC ..... A61B 6/025; G06T 11/005; G06T 11/008; G06T 2207/10081; G06T 2207/10116; G06T 2207/20081; G06T 2211/436
See application file for complete search history.

(56) References Cited

U.S. PATENT DOCUMENTS

| | | |
|---|---|---|
| 9,332,953 B2 | 5/2016 | Suzuki |
| 9,595,120 B2 | 3/2017 | Nguyen et al. |
| 2017/0071562 A1 | 3/2017 | Suzuki |

FOREIGN PATENT DOCUMENTS

EP 3 435 334 1/2019

OTHER PUBLICATIONS

Jiwon Kim et al., "Accurate Image Super-Resolution Using Very Deep Convolutional Networks", CVPR, 2016, pp. 1646-1654.
(Continued)

*Primary Examiner* — Edward Park
(74) *Attorney, Agent, or Firm* — Staas & Halsey LLP

(57) ABSTRACT

Provided are a method and apparatus for interpolating X-ray tomographic image data by using a machine learning model. A method of interpolating an X-ray tomographic image or X-ray tomographic composite image data includes obtaining a trained model parameter via machine learning that uses a sub-sampled sinogram for learning as an input and uses a full-sampled sinogram for learning as a ground truth; radiating X-rays onto an object at a plurality of preset angular locations via an X-ray source, and obtaining a sparsely-sampled sinogram including X-ray projection data obtained via X-rays detected at the plurality of preset angular locations; applying the trained model parameter to the sparsely-sampled sinogram by using the machine learning model; and generating a densely-sampled sinogram by estimating X-ray projection data not obtained with respect to the object on the sparsely-sampled sinogram.

23 Claims, 16 Drawing Sheets

(52) U.S. Cl.
CPC .............. *G06T 2207/10081* (2013.01); *G06T 2207/10116* (2013.01); *G06T 2207/20081* (2013.01); *G06T 2211/436* (2013.01)

(56) References Cited

OTHER PUBLICATIONS

Hua Zhang et al., "Directional sinogram interpolation for sparse angular acquisition in cone-beam computed tomography", Journal of X-Ray Science and Technology 21 (2013), Sep. 10, 2013, pp. 481-496.

Hoyeon Lee et al. "View-interpolation of sparsely sampled sonogram using convolutional neural network" Progress in Biomedical Optics and Imaging, SPIE—International Society for Optical Engineering, Bellingham, WA, US, vol. 10133, Feb. 24, 2017, XP060086962.

Extended European Search Report dated Apr. 5, 2019 in corresponding European Patent Application No. 18204643.3.

METHOD AND APPARATUS FOR GENERATING X-RAY TOMOGRAPHIC IMAGE DATA

CROSS-REFERENCE TO RELATED APPLICATION(S)

This application is based on and claims priority under 35 U.S.C. § 119 to Korean Patent Application No. 10-2017-0146945, filed on Nov. 6, 2017, in the Korean Intellectual Property Office, the disclosure of which is incorporated by reference herein in its entirety.

BACKGROUND

1. Field

The disclosure relates to a method and apparatus for generating X-ray tomographic image data, and more particularly, to a method and apparatus for interpolating X-ray projection data by using machine learning in a computed tomography (CT) apparatus or a tomosynthesis imaging apparatus.

2. Description of the Related Art

Medical imaging apparatuses are equipment for capturing an image of an internal structure of an object. Medical imaging apparatuses are noninvasive examination apparatuses that capture and process images of the structural details of a human body, internal tissue thereof, and fluid flow therein and provide the processed images to a user. A user, such as a doctor, may diagnose a health state and a disease of a patient by using a medical image output from a medical imaging apparatus.

Representative examples of apparatuses for radiating X-rays onto a patient to scan an object include computed tomography (CT) apparatuses. CT apparatuses are capable of providing a cross-sectional image of an object and distinctively expressing inner structures (e.g., organs such as a kidney, a lung, etc.) of the object, compared to general X-ray apparatuses. Thus, CT apparatuses are widely used for accurately diagnosing a disease.

CT apparatuses may detect an X-ray transmitted through an object by using an X-ray detector and may perform image processing on X-ray projection data obtained using the detected X-ray, thereby reconstructing an accurate CT image. In general, many X-ray projection images, each of which is an input image, should be densely obtained to increase the reconstruction image quality of an X-ray tomographic image. However, in this case, the number of X-ray projection images to be obtained increases, and thus much time is taken to obtain the X-ray projection images, and the number of X-rays projected onto an object, namely, a patient, relatively increases. Medical images using X-rays may cause X-ray exposure, and, when the obtainment time increases, a patient may move, inevitably leading to degradation in the image quality of reconstructed CT images. Thus, a high-performance reconstruction technology is required to obtain a high-definition CT image and also reduce the number of X-ray projection images. A method of obtaining a sparsely-sampled projection image, transforming the sparsely-sampled projection image into a densely-sampled projection image via linear interpolation or the like, and reconstructing a three-dimensional (3D) image by using the densely-sampled projection image has recently become well known.

SUMMARY

Provided are a method and apparatus for interpolating an obtained X-ray projection image of an object via machine learning and reconstructing a high-definition X-ray tomographic image via the interpolated X-ray projection image, within a computed tomography (CT) apparatus. The embodiments of the present disclosure are applicable to a tomosynthesis imaging apparatus.

Additional aspects will be set forth in part in the description which follows and, in part, will be apparent from the description, or may be learned by practice of the presented embodiments.

In accordance with an aspect of the disclosure, a method of interpolating an X-ray tomographic image or X-ray tomographic composite image data includes obtaining a trained model parameter via machine learning that uses a sub-sampled sinogram for learning as an input and uses a full-sampled sinogram for learning as a ground truth; radiating X-rays onto an object at a plurality of preset angular locations via an X-ray source, and obtaining a sparsely-sampled sinogram including X-ray projection data obtained via X-rays detected at the plurality of preset angular locations; applying the trained model parameter to the sparsely-sampled sinogram by using the machine learning model; and generating a densely-sampled sinogram by estimating X-ray projection data not obtained with respect to the object on the sparsely-sampled sinogram.

The method may further include interpolating the sparsely-sampled sinogram via linear interpolation before applying the trained model parameter to the sparsely-sampled sinogram.

The applying of the trained model parameter may include cropping the sparsely-sampled sinogram into at least one image patch; applying the trained model parameter by inputting the at least one image patch to the machine learning model including a plurality of layers; and estimating X-ray projection data not obtained and thus not included in the sparsely-sampled sinogram, by applying the trained model parameter.

The method may further include maintaining a value of trained X-ray projection data at the plurality of angular locations to be equal to a value of X-ray projection data obtained at angles corresponding to the plurality of angular locations included in the sparsely-sampled sinogram initially provided as an input.

The method may further include obtaining a residual sinogram that is a difference between the densely-sampled sinogram generated via the training and the sparsely-sampled sinogram input to the machine learning model.

The maintaining may include applying, to the residual sinogram, a base projection data preserving layer that maintains the value of the trained X-ray projection data at the plurality of angular locations to be equal to the value of the X-ray projection data obtained at angles corresponding to the plurality of angular locations included in the sparsely-sampled sinogram; and adding the sparsely-sampled sinogram initially provided as an input to the residual sinogram to which the base projection data preserving layer has been applied. The base projection data preserving layer may process a pixel value of at least one piece of X-ray projection data obtained at the plurality of angular locations to be 0.

The maintaining may include applying a base projection data maintaining layer that replaces a pixel value of at least one piece of X-ray projection data obtained at the plurality of angular locations with the value of the X-ray projection data obtained at the angles corresponding to the plurality of angular locations included in the sparsely-sampled sinogram initially provided as an input. The applying of the base projection data preserving layer may be performed after the adding of the sparsely-sampled sinogram initially provided as an input to the residual sinogram.

The method may further include cropping the sparsely-sampled sinogram into one or more image patches each having a length equal to a sensor size of an X-ray detector in a first direction and a preset width in a second direction perpendicular to the first direction. The applying of the trained model parameter may include applying the trained model parameter by inputting each of the one or more image patches to the machine learning model.

The method may further include equalizing a sum of pieces of X-ray projection data obtained at a same angular location from among one or more pieces of X-ray projection data included in the densely-sampled sinogram to a sum of pieces of X-ray projection data obtained at an angle corresponding to the same angular location on the sparsely-sampled sinogram input to the machine learning model.

The equalizing of the sum of the obtained pieces of X-ray projection data may include interpolating values of trained pieces of X-ray projection data, based on a sum of pieces of X-ray projection data obtained at a first angular location on the densely-sampled sinogram and a sum of pieces of X-ray projection data obtained at a second angular location that is adjacent to the first angular location.

The method may further include applying the trained model parameter by inputting the densely-sampled sinogram to the machine learning model, and training the densely-sampled sinogram via the trained model parameter. Resolution of the densely-sampled sinogram may be increased by performing the training by applying the trained model parameter to the trained densely-sampled sinogram a plurality of times.

In accordance with another aspect of the disclosure, a computed CT imaging apparatus that interpolates X-ray tomographic image data includes an X-ray source configured to radiate X-rays to an object at a plurality of present angular locations; an X-ray detector configured to detect X-rays radiated by the X-ray source and transmitted by the object; a data acquisition system (DAS) configured to obtain a sparsely-sampled sinogram of the object from the X-rays detected by the X-ray detector; and a processor configured to generate a densely-sampled sinogram by obtaining a trained model parameter via training using a machine learning model that uses a sub-sampled sinogram for learning as an input and uses a full-sampled sinogram for learning as a ground truth, applying the trained model parameter to the sparsely-sampled sinogram obtained by the DAS by using the machine learning model, and estimating X-ray projection data not obtained with respect to the object on the sparsely-sampled sinogram.

The processor may be further configured to interpolate the sparsely-sampled sinogram via linear interpolation before applying the trained model parameter to the sparsely-sampled sinogram.

The processor may be further configured to crop the sparsely-sampled sinogram into at least one image patch, apply the trained model parameter by inputting each of the at least one image patch to the machine learning model, and obtain a densely-sampled sinogram generated via the training.

The processor may be further configured to maintain a value of X-ray projection data obtained at the plurality of angular locations to be equal to a value of X-ray projection data obtained at angles corresponding to the plurality of angular locations included in the sparsely-sampled sinogram initially provided as an input.

The processor may be further configured to obtain a residual sinogram that is a difference between the densely-sampled sinogram generated via the training and the sparsely-sampled sinogram input to the machine learning model.

The processor may be further configured to apply, to the residual sinogram, a base projection data preserving layer that maintains the value of the trained X-ray projection data at the plurality of angular locations to be equal to the value of the X-ray projection data obtained at angles corresponding to the plurality of angular locations included in the sparsely-sampled sinogram, and add the sparsely-sampled sinogram initially provided as an input to the residual sinogram to which the base projection data preserving layer has been applied. The base projection data preserving layer may process a pixel value of at least one piece of X-ray projection data obtained at the plurality of angular locations to be 0.

The processor may be further configured to apply a base projection data preserving layer that replaces a pixel value of at least one piece of X-ray projection data obtained at the plurality of angular locations with the value of the X-ray projection data obtained at the angles corresponding to the plurality of angular locations included in the sparsely-sampled sinogram initially provided as an input. The base projection data preserving layer may be applied after the sparsely-sampled sinogram initially provided as an input is added to the residual sinogram.

The processor may be further configured to crop the sparsely-sampled sinogram into one or more image patches each having a length equal to a sensor size of an X-ray detector in a first direction and a preset width in a second direction perpendicular to the first direction, and apply the trained model parameter by inputting each of the at least one image patch to the machine learning model.

The processor may be further configured to equalize a sum of pieces of X-ray projection data obtained at a same angular location from among one or more pieces of X-ray projection data included in the densely-sampled sinogram to a sum of pieces of X-ray projection data obtained at an angular location corresponding to the same angular location on the sparsely-sampled sinogram input to the machine learning model.

The processor may be further configured to interpolate values of trained pieces of X-ray projection data, based on a sum of pieces of X-ray projection data obtained at a first angular location on the densely-sampled sinogram and a sum of pieces of X-ray projection data obtained at a second angular location that is adjacent to the first a angular location.

The processor may be further configured to apply the trained model parameter by inputting the densely-sampled sinogram to the machine learning model, train the densely-sampled sinogram via the trained model parameter, and perform the training by applying the trained model parameter to the trained densely-sampled sinogram a plurality of times to increase resolution of the densely-sampled sinogram.

In accordance with another aspect of the disclosure, a computer program product includes a computer-readable storage medium having a computer-readable program stored therein. The computer-readable program, when executed on a computing device, causes the computing device to obtain a trained model parameter via training using a machine learning model that uses a sub-sampled sinogram for learning as an input and uses a full-sampled sinogram for learning as a ground truth; obtain a sparsely-sampled sinogram including X-ray projection data obtained via X-rays radiated onto an object at a plurality of preset angular locations via an X-ray source and detected at the plurality of preset angular locations; apply the trained model parameter to the sparsely-sampled sinogram by using the machine learning model; and generate a densely-sampled sinogram by estimating X-ray projection data not obtained with respect to the object on the sparsely-sampled sinogram.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
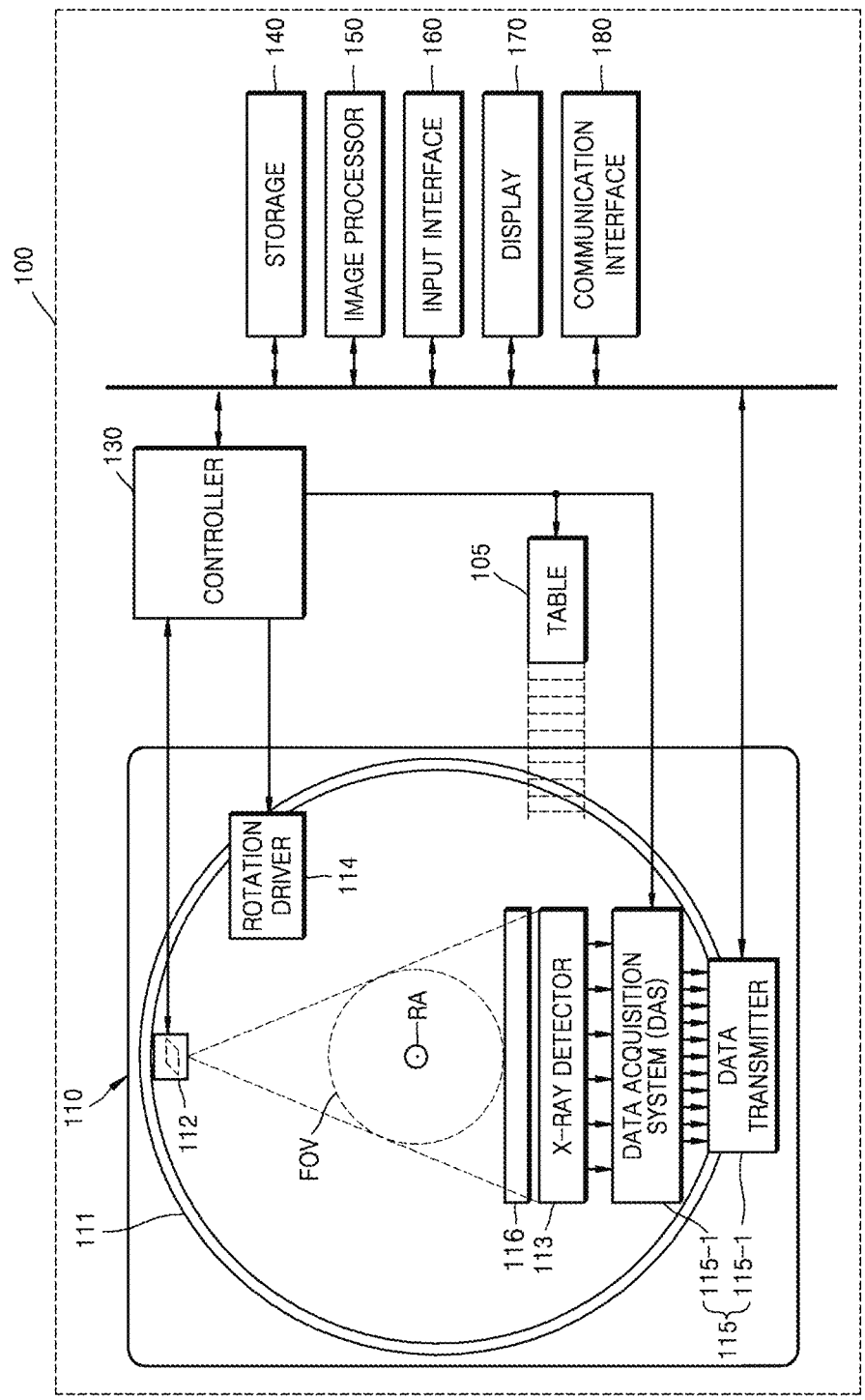
FIG. 1 illustrates a structure of a computed tomography (CT) system according to an embodiment.

The principle of the disclosure is explained and embodiments are disclosed so that the scope of the disclosure is clarified and one of ordinary skill in the art to which the present disclosure pertains may implement the disclosure. The disclosed embodiments may have various forms.

Throughout the specification, like reference numerals or characters refer to like elements. In the present specification, all elements of embodiments are not explained, but general matters in the technical field of the disclosure or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

FIG. 1 illustrates a structure of a CT system 100 according to an embodiment.

The CT system 100 may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program codes for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to an embodiment, the tomography data may be in the form of data that has undergone back-projection, or in the form of a tomography image. According to embodiments, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The input interface 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smart-phone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

The communication interface 180 may receive control signals and data from an external device and transmit the received control signals to the controller 130 so that the controller 130 may control the CT system 100 according to the received control signals.

Alternatively, by transmitting a control signal to an external device via the communication interface 180, the controller 130 may control the external device according to the control signal.

For example, the external device may process data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides an application may include a recording medium having the program recorded thereon.

According to embodiments, the CT system 100 may or may not use contrast media during a CT scan, and may be implemented as a device connected to other equipment.

Figure 2:
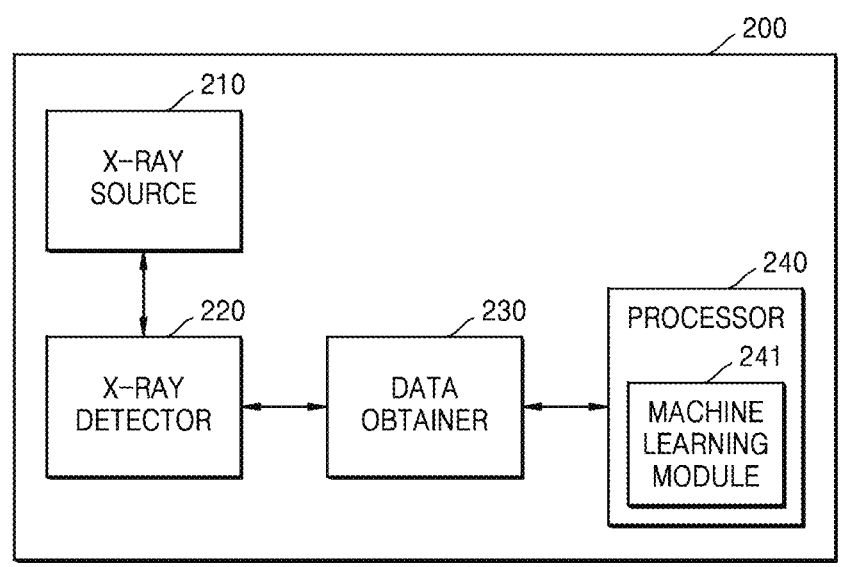
FIG. 2 is a block diagram of a CT imaging apparatus according to an embodiment.

FIG. 2 is a block diagram of a CT imaging apparatus 200 according to an embodiment of the present disclosure. In the entire specification as well as FIG. 2, the CT imaging apparatus 200 may be a tomosynthesis imaging apparatus that synthesizes CT images. In the entire specification, the CT imaging apparatus 200 may synthesize CT images, or train CT images via a machine learning model and then synthesize the trained CT images.

Referring to FIG. 2, the CT imaging apparatus 200 may include an X-ray source 210, an X-ray detector 220, a data obtainer 230, and a processor 240. The CT imaging apparatus 200 of FIG. 2 may be the same as the CT system 100 of FIG. 1. Because FIG. 2 illustrates only essential components of the CT imaging apparatus 200 according to an embodiment of the present disclosure, the CT imaging apparatus 200 may further include the gantry 110, the table 105, the input interface 160, the display 170, and the communication interface 180 of FIG. 1.

The X-ray source 210 may generate X-rays, and may radiate the generated X-rays to an object (for example, a patient) while rotating on the rotating frame 111 of FIG. 1 arranged around the object. According to an embodiment, the X-ray source 210 may radiate X-rays onto the object at a plurality of angles while rotating about the rotation axis RA of FIG. 1 on the rotating frame 111 at intervals of a preset angle. For example, the X-ray source 210 may radiate X-rays onto the object while rotating about a rotation axis at intervals of 4°. In this case, the X-ray source 210 may radiate X-rays onto the object at locations corresponding to angles 1°, 5°, 9°, and the like.

The X-ray detector 220 may detect the X-rays radiated onto the object via the X-ray source 210 at a plurality of angular locations. The X-ray detector 220 may detect the radiated X-rays by using a scintillator, a photon counting detector, or the like. The X-ray detector 220 may detect the X-rays radiated at a plurality of angular locations at which the X-ray source 210 rotates. For example, when the X-ray source 210 radiates X-rays onto the object at angles of 1°, 5°, 9°, and the like, the X-ray detector 220 may detect X-rays according to the angles of 1°, 5°, 9°, and the like.

The data obtainer 230 may obtain X-ray projection data output by the X-ray detector 220. The data obtainer 230 may include at least one amplification circuit, and may amplify the X-ray projection data by using the at least one amplification circuit. The data obtainer 230 of FIG. 2 may be the same component as the DAS 115-1 of FIG. 1.

According to an embodiment, the data obtainer 230 may obtain a sparsely-sampled sinogram from the X-ray detector 220 that has detected the X-rays that the X-ray source 210 radiated at the plurality of angular locations while rotating at intervals of a preset angle with respect to an axis having the object at its center.

A sinogram means a sequential stack of X-ray projection images each including X-ray projection data obtained via X-rays detected for each angle at which the rotating X-ray source is located. The sinogram may have directivity that is similar to sine waves. The sparsely-sampled sinogram means a sinogram obtained by the X-ray source 210 radiating X-rays at only preset angles, instead of radiating X-rays at all angles by rotating 360° about the rotating axis, and detecting the X-rays at only the radiation angles. Thus, the sparsely-sampled sinogram is defined as a sinogram including only some pieces of sparsely-obtained data of the object instead of including all pieces of data of the object when reconstructing a CT image.

The processor 240 may obtain a model parameter via training using a machine learning model using a plurality of images as an input and using an image to be trained as a ground truth. The machine learning (ML) model means a technique of expressing image data or the like in a vector, graph, or the like, which is a format processible by a computer, and training the image data or the like to establish a model parameter. According to the present disclosure, the machine learning model may include, but is not limited to, an artificial neural network (ANN), a support vector machine (SVM), or a deep learning network. Embodiments of the present disclosure may be implemented using all machine learning methods well known in the machine learning model field.

According to an embodiment, a deep learning network, which is a field of the machine learning model, may include a well-known deep learning technique, such as a convolution neural network (CNN), or a rectified linear unit (ReLU).

The processor 240 may include a hardware unit having a computation capability that performs algorithms of all machine learning models including an ANN model, an SVM, and deep learning and applications associated with the algorithms. For example, the processor 240 may include at least one of a central processing unit (CPU), a microprocessor, and a graphics processing unit (GPU). According to an embodiment, the processor 240 may include a machine learning module 241 that executes a machine learning model and performs training by applying a model parameter to an input image. In FIG. 2, the processor 240 includes the machine learning module 241; however embodiments of the present disclosure are not limited thereto. According to an embodiment, the processor 240 and the ML module 241 may be integrated into a single chip, instead of being formed as independent modules. Although not shown in FIG. 2, the CT imaging apparatus 200 may further include a memory that stores a machine learning model algorithm or application that is performed by the processor 240.

The processor 240 may apply a trained model parameter to the sparsely-sampled sinogram obtained by the data obtainer 230 by using the machine learning model. According to an embodiment, the processor 240 may interpolate the sparsely-sampled sinogram via linear interpolation before applying the trained model parameter to the sparsely-sampled sinogram.

The processor 240 may perform training of estimating X-ray projection data about the object not included in the sparsely-sampled sinogram via a machine learning model of applying a model parameter to the sparsely-sampled sinogram. The processor 240 may generate a densely-sampled sinogram via the training. According to the present disclosure, because the X-ray source 210 radiates X-rays at only a plurality of preset angular locations and the X-ray detector 220 detects only the radiated X-rays, non-obtained X-ray projection data is estimated via training via a machine learning model and the densely-sampled sinogram means a sinogram interpolated by using the estimated value of the X-ray projection data.

According to an embodiment, the processor 240 may crop the sparsely-sampled sinogram into one or more image patches, and perform training by inputting each of the plurality of image patches to the machine learning model. The processor 240 may apply the model parameter trained via the machine learning model and may estimate not-obtained X-ray projection data on the sparsely-sampled sinogram.

According to an embodiment, the processor 240 may generate the densely-sampled sinogram via training via the machine learning model, and may obtain a residual sinogram, which is a difference between the generated densely-sampled sinogram and the sparsely-sampled sinogram initially input to the machine learning model. This method will be described in detail with reference to FIGS. 5 and 6.

According to an embodiment, the processor 240 may apply, to the machine learning model, a base projection data preserving layer that preserves the values of one or more pieces of X-ray projection data obtained at a plurality of angular locations on the residual sinogram to be equal to the values of one or more pieces of X-ray projection data obtained at corresponding angles on the initially-input sparsely-sampled sinogram. This will be described in greater detail later with reference to FIGS. 7 and 8.

According to an embodiment, the processor 240 may crop the sparsely-sampled sinogram into one or more image patches each having a length equal to a sensor size of the X-ray detector 220 in a first direction and a preset width in a second direction perpendicular to the first direction. The processor 240 may apply the trained model parameter by inputting each of the one or more image patches to the machine learning model. This will be described in greater detail later with reference to FIG. 9.

According to an embodiment, the processor 240 may apply, to a finally generated densely-sampled sinogram, a projection sum preserving layer that equalizes a sum of pieces of X-ray projection data obtained at the same angle from among the one or more pieces of X-ray projection data generated via training to a sum of pieces of X-ray projection data obtained at the corresponding angle on the initially obtained sparsely-sampled sinogram. This will be described in greater detail later with reference to FIG. 10.

According to an embodiment, the processor 240 may perform a plurality of times a training operation of applying a model parameter by using the densely-sampled sinogram trained via the machine learning model as an input of the machine learning model again. The processor 240 may increase resolution of the sparsely-sampled sinogram according to a method of connecting machine learning models in a cascade manner and making the sparsely-sampled sinogram pass through the connected machine learning models. This will be described in greater detail later with reference to FIGS. 11 and 12.

Examples of a general method of interpolating an X-ray projection image, namely, a sinogram, may include interpolation via an analytic technique in consideration of directivity of a sinogram. A method related with the interpolation is recited in the thesis of Hua Zhang, Directional sinogram interpolation for sparse angular acquisition in cone-beam computed tomography, Hua Zhang, 2013.09. However, because the method recited in the thesis is not generating meaningful information, based on statistical characteristics of a sinogram, the method recited in the thesis provides decreased resolution and a bad-quality reconstructed CT image, compared with actual obtainment of a dense sinogram or a full-sampled sinogram.

There is provided the CT imaging apparatus 200 that trains a sparsely-sampled sinogram including only the X-ray projection data obtained at a plurality of angles by using a machine learning model, and estimates X-ray projection data not obtained on the sparsely-sampled sinogram to thereby generate a densely-sampled sinogram that is meaningful not only in respect of an analytic approach but also in a statistical respect. Therefore, the CT imaging apparatus 200 according to an embodiment of the present disclosure may increase the image quality of a reconstructed CT image.

Figure 3:
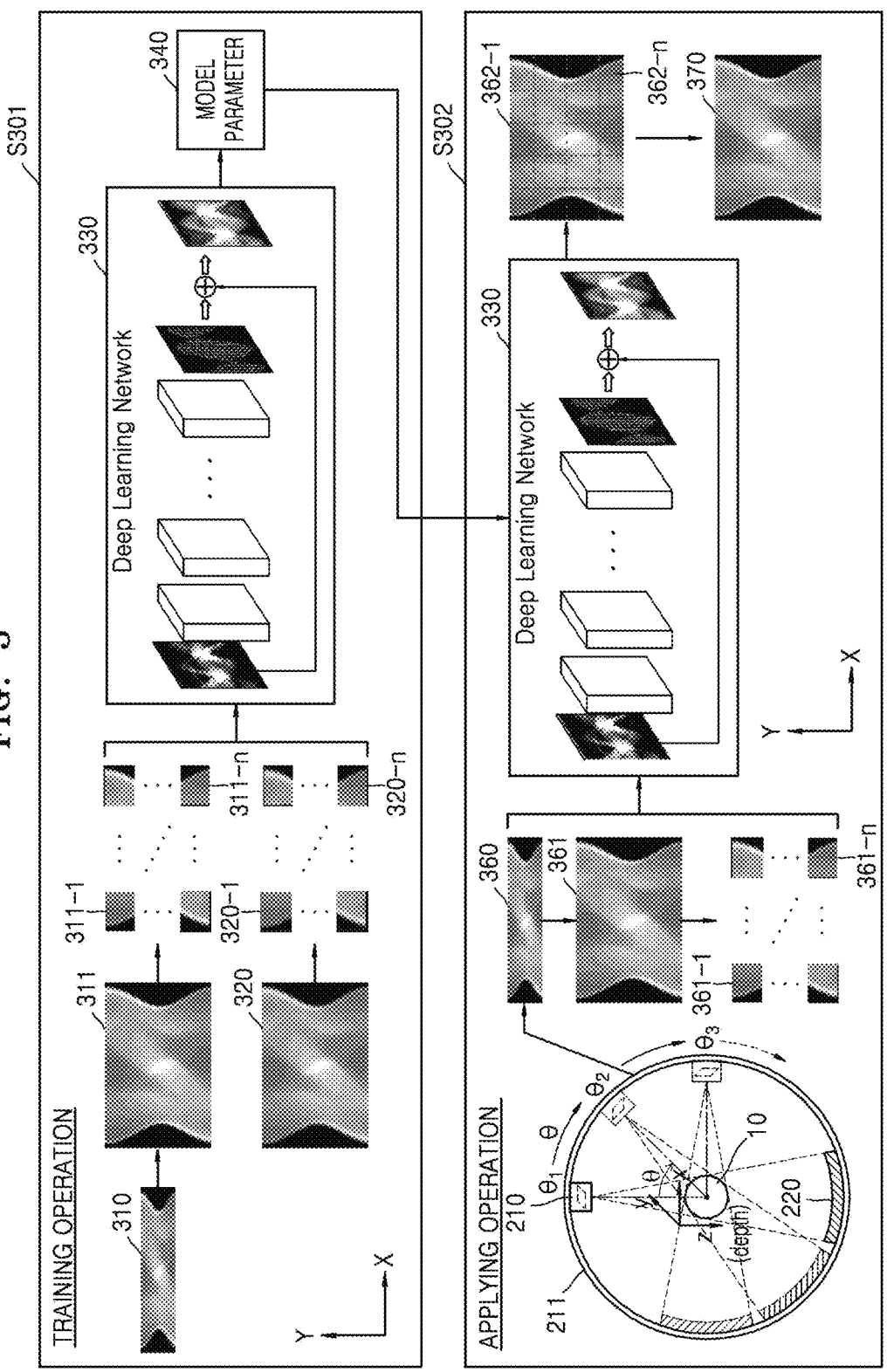
FIG. 3 is a conceptual view for explaining a method, performed by a CT imaging apparatus according to an embodiment, of interpolating an X-ray projection image by using machine learning.

FIG. 3 is a conceptual view for explaining a method in which a CT imaging apparatus according to an embodiment of the present disclosure interpolates an X-ray projection image by using machine learning. All embodiments illustrated in FIG. 3 may be equally performed not only in a CT imaging apparatus but also in a tomosynthesis imaging apparatus.

Referring to FIG. 3, the CT imaging apparatus may perform training operation S301 of training a model parameter 340, and applying operation S302 of generating a densely-sampled sinogram 370 by applying the trained model parameter 340 to a sparsely-sampled sinogram 360.

In training operation S301, the CT imaging apparatus may obtain the model parameter 340 via a machine learning model 330 that uses a sub-sampled sinogram 310 as an input and uses a full-sampled sinogram 320 as a ground truth. The sub-sampled sinogram 310 means an X-ray projection image including only X-ray projection data obtained at a plurality of preset angles with respect to an object instead of including X-ray projection data obtained at all angles with respect to the object. The full-sampled sinogram 320 means an X-ray projection image including all pieces of X-ray projection data obtained by detecting X-rays radiated at all angles, namely, each of 360°, with respect to the object.

The CT imaging apparatus generates an interpolated sub-sampled sinogram 311 by interpolating the sub-sampled sinogram 310 via linear interpolation (LI) or the like. However, the interpolating method is not limited to LI. According to an embodiment, the CT imaging apparatus may interpolate the sub-sampled sinogram 310, via at least one of spline interpolation, polynomial interpolation, and already-well-known interpolation methods.

The CT imaging apparatus may crop the interpolated sub-sampled sinogram 311 and the full-sampled sinogram 320 into one or more image patches 311-1 through 311-$n$ and one or more image patches 320-1 through 320-$n$, respectively. According to an embodiment, the CT imaging apparatus may crop the interpolated sub-sampled sinogram 311 and the full-sampled sinogram 320 into the one or more image patches 311-1 through 311-$n$ and the one or more image patches 320-1 through 320-$n$, respectively, having the same sizes. Although FIG. 3 illustrates a plurality of image patches 311-1 through 311-$n$ and a plurality of image patches 320-1 and 320-$n$, embodiments are not limited thereto. According to an embodiment, each image patch may have the same size as that of a not-yet-cropped sinogram, namely, each of the interpolated sub-sampled sinogram 311 and the full-sampled sinogram 320.

The CT imaging apparatus may perform training via a machine learning model that uses the plurality of image patches 311-1 through 311-$n$ of the interpolated sub-sampled sinogram 311 as an input and uses the plurality of image patches 320-1 through 320-$n$ of the full-sampled sinogram 320 as a ground truth. According to an embodiment, the machine learning model may include at least one of an ANN, an SVM, and a deep learning network. The CT imaging apparatus according to the present disclosure may use all of currently-well-known machine learning models. The CT imaging apparatus may train a model parameter via a machine learning model.

In applying operation S302, the CT imaging apparatus may radiate X-rays onto an object 10 at locations corresponding to a plurality of angles θ1, θ2, θ3, and the like while rotating the X-ray source 210 along the rotating frame 211 formed around the object 10 at intervals of a preset angle θ. The X-rays radiated by the X-ray source 210 may be detected by the X-ray detector 220 while passing through the object 10. The X-ray detector 220 may transmit the detected X-rays to the data obtainer 230 of FIG. 2, and the data obtainer 230 may obtain X-ray projection data. The obtained X-ray projection data is an image including pieces of X-ray projection data obtained by detecting only X-rays radiated at locations corresponding to the plurality of preset angles θ1, θ2, θ3, and the like instead of detecting X-rays while rotating around the object 10 by 360°, and accordingly may be the sparsely-sampled sinogram 360.

The CT imaging apparatus may generate an interpolated sparsely-sampled sinogram 361 by interpolating the sparsely-sampled sinogram 360 via linear interpolation or the like. An interpolating method used by the CT imaging apparatus is not limited to linear interpolation. According to an embodiment, the CT imaging apparatus may interpolate the sparsely-sampled sinogram 360, via at least one of spline interpolation, polynomial interpolation, and already-well-known interpolation methods.

The CT imaging apparatus may crop the interpolated sparsely-sampled sinogram 361 into one or more image patches 361-1 through 361-$n$ each having a preset size. According to an embodiment, each of the obtained one or more image patches 361-1 through 361-$n$ may have the same size as each of the one or more image patches 311-1 through 311-$n$ and 320-1 through 320-$n$ obtained in training operation S301. However, embodiments are not limited thereto.

The CT imaging apparatus may apply the trained model parameter 340 to the one or more image patches 361-1 through 361-$n$ via the machine learning model 330. The CT imaging apparatus may generate one or more trained image patches 362-1 through 362-$n$ by performing training by applying the model parameter 340 to the one or more image patches 361-1 through 361-$n$.

The CT imaging apparatus may finally generate the densely-sampled sinogram 370 by performing tiling by sticking the one or more trained image patches 362-1 through 362-$n$ together in the cropping order. The densely-sampled sinogram 370 may include estimated data obtained by estimating, via training using a machine learning model, pieces of X-ray projection data not obtained because they do not correspond to the preset angles and accordingly not included in the sparsely-sampled sinogram 360.

Figure 4:
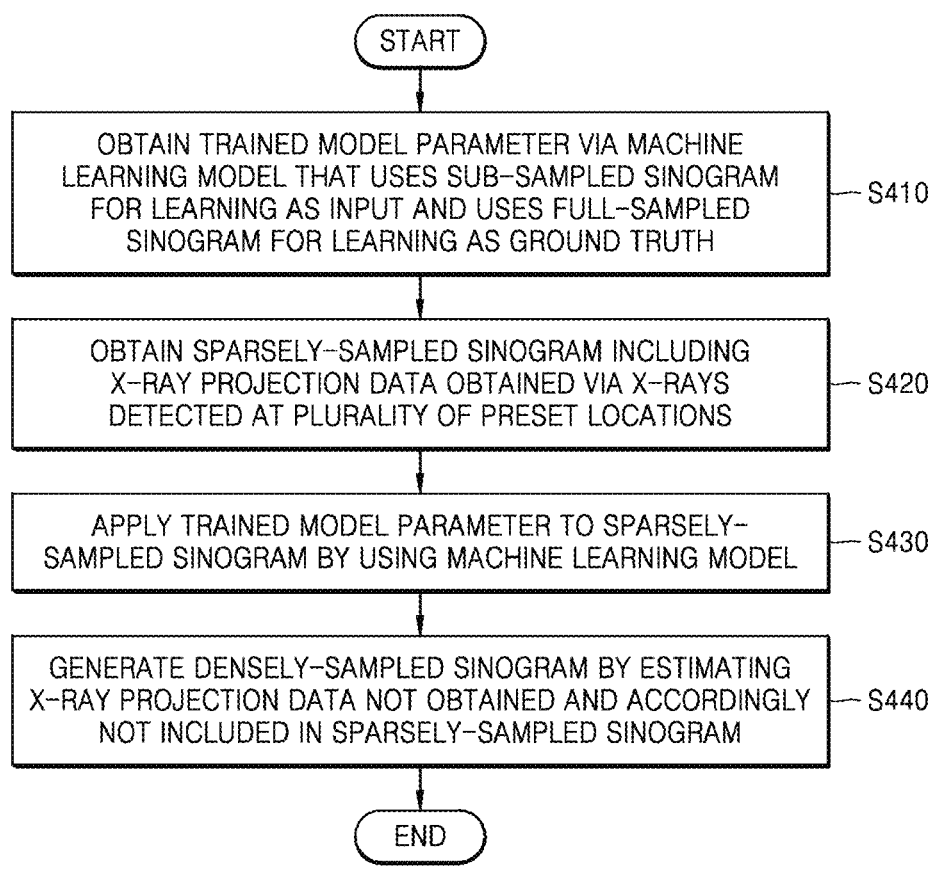
FIG. 4 is a flowchart of a method, performed by a CT imaging apparatus according to an embodiment, of interpolating an X-ray projection image by using machine learning.

FIG. 4 is a flowchart of a method in which a CT imaging apparatus according to an embodiment of the present disclosure interpolates an X-ray projection image by using machine learning. All operations illustrated in FIG. 4 may be performed equally not only in a CT imaging apparatus but also in a tomosynthesis imaging apparatus.

In operation S410, the CT imaging apparatus obtains a model parameter via training using a machine learning model that uses a sub-sampled sinogram for learning as an input and uses a full-sampled sinogram for learning as a ground truth. The sub-sampled sinogram for learning means a sinogram including X-ray projection data obtained by radiating X-rays onto the same object at only preset angles, and the full-sampled sinogram for learning means X-ray projection data obtained by radiating X-rays onto the same object at all angles. The sub-sampled sinogram for learning and the full-sampled sinogram for learning are related with the same object and thus may make a pair.

According to an embodiment, for convenience in a training operation, the input sub-sampled sinogram for learning and the input full-sampled sinogram for learning may be cropped into image patches each having a certain size. These image patches may be obtained from various types of sub-sampled sinograms for learning, and several tens to several hundreds of image patches may be applied as an input according to the type and characteristics of an image to be reconstructed.

According to an embodiment, the machine learning model that is applied includes at least one of an ANN, an SVM, and a deep learning network. However, embodiments are not limited thereto. All methods and algorithms well known in the machine learning field are applicable.

In operation S420, the CT imaging apparatus obtains a sparsely-sampled sinogram including X-ray projection data obtained via X-rays radiated by an X-ray source at a plurality of preset locations and detected at the plurality of preset locations. According to an embodiment, the CT imaging apparatus rotates the X-ray source at intervals of a preset angle, and obtains a sparsely-sampled sinogram including one or more pieces of X-ray projection data obtained via X-rays detected by an X-ray detector at a plurality of angular locations. For example, when the X-ray source radiates X-rays onto an object while rotating at angles of 1°, 5°, 9°, and the like on a rotating frame, the X-ray detector may detect X-rays at locations corresponding to the angles of 1°, 5°, 9°, and the like. In this case, a DAS may obtain one or more pieces of X-ray projection data from the X-rays detected at the locations corresponding to the angles of 1°, 5°, 9°, and the like, and may also obtain a sparsely-sampled sinogram which is a stack of the one or more pieces of X-ray projection data according to the angles.

In operation S430, the CT imaging apparatus applies the trained model parameter to the sparsely-sampled sinogram by using the machine learning model. The trained model parameter, which is obtained in operation S410, may be a feature value representing a relationship between the sub-sampled sinogram for learning and the full-sampled sinogram for learning.

According to an embodiment, the CT imaging apparatus may apply the trained model parameter to the sparsely-sampled sinogram via the machine learning model.

In operation S440, the CT imaging apparatus generates a densely-sampled sinogram by estimating X-ray projection data not obtained and accordingly not included in the sparsely-sampled sinogram. According to an embodiment, the CT imaging apparatus may generate the final densely-sampled sinogram by cropping the sparsely-sampled sinogram into one or more image patches, applying the model parameter to the one or more image patches, and tiling the one or more image patches trained using the applied model parameter.

Figure 5:
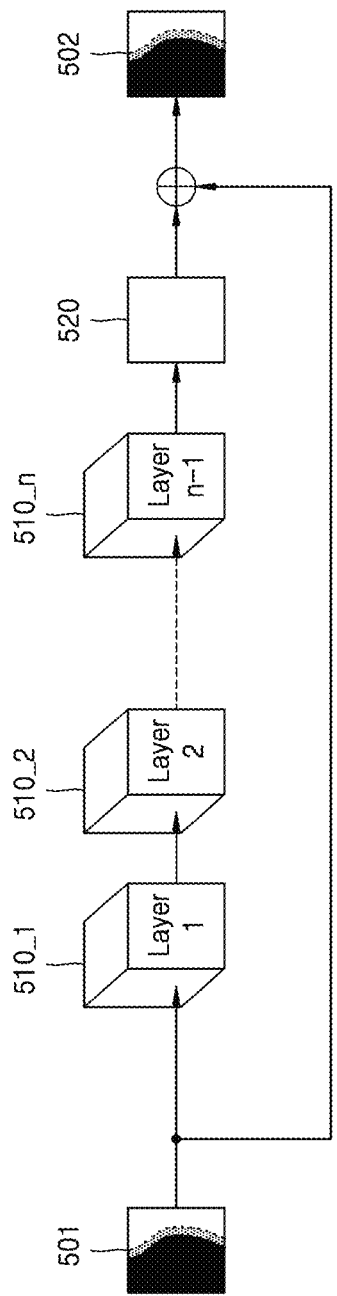
FIG. 5 is a conceptual view for explaining a method, performed by a CT imaging apparatus according to an embodiment, of interpolating an X-ray projection image by using a machine learning model.

FIG. 5 is a conceptual view for explaining a method in which a CT imaging apparatus according to an embodiment of the present disclosure interpolates an X-ray projection image by using a machine learning model. The interpolation of the X-ray projection image by using the machine learning model shown in FIG. 5 may be equally performed not only in a CT imaging apparatus but also in a tomosynthesis imaging apparatus.

Referring to FIG. 5, the CT imaging apparatus may train an image patch 501 of a sparsely-sampled sinogram by inputting the image patch 501 to a machine learning model, and may generate a densely-sampled sinogram 502 via the training. The image patch 501 may be an image in which the sparsely-sampled sinogram is cropped into a plurality of patches having a preset size, but embodiments are not limited thereto. According to an embodiment, the image patch 501 may be an image having the same size as the sparsely-sampled sinogram. In other words, the CT imaging apparatus may input the sparsely-sampled sinogram to the machine learning model without cropping the sparsely-sampled sinogram, and apply the model parameter to the machine learning model, to thereby train the sparsely-sampled sinogram.

The machine learning model of FIG. 5 may be implemented using at least one of an ANN, an SVM, and a deep learning network each having a plurality of layers 510_1 through 510_$n$ but embodiments are not limited thereto. In other words, the CT imaging apparatus may train a sparsely-sampled sinogram by applying all machine learning models and algorithms well known in the machine learning field, and may interpolate the trained sparsely-sampled sinogram into a densely-sampled sinogram.

First of all, the CT imaging apparatus interpolates the sparsely-sampled sinogram via linear interpolation and crops the interpolated sparsely-sampled sinogram to generate the image patch 501.

The CT imaging apparatus may use the image patch 501 as an input of the machine learning model including the plurality of layers 510_1 through 510_n. The plurality of layers 510_1 through 510_n may be layers having a weighting factor that is used in all machine learning models or algorithms well known in the machine learning field. According to an embodiment, the plurality of layers 510_1 through 510_n may be convolution layers that generate a feature map by using a filter F_1 having a preset number of channels, n. In this case, the CT imaging apparatus may extract a feature value by using a filter having a preset size, for example, a 3×3 size, and including 64 channels, from the image patch 501, and stride the filter to thereby generate a feature map for the entire image patch 501. However, the 3×3 size of the filter and the number of channels, n, included in the filter are merely examples, and embodiments are not limited thereto.

The CT imaging apparatus may perform training by applying weights to the image patch 501 while making the image patch 501 sequentially pass through the first layer 510_1, the second layer 510_2, ..., through to the n-th layer 510_n, and updating the weights.

According to an embodiment, the CT imaging apparatus may obtain a residual sinogram 520 by again performing filtering on a final weight calculated by passing through the n-th layer 510_n. The residual sinogram 520 may be an X-ray projection image that means a difference between the densely-sampled sinogram 502 generated via training and the image patch 501 of the sparsely-sampled sinogram input to the machine learning model. Ideally, when training via the machine learning model is perfectly performed, all pixel values of the residual sinogram 520 may be 0.

Figure 6:
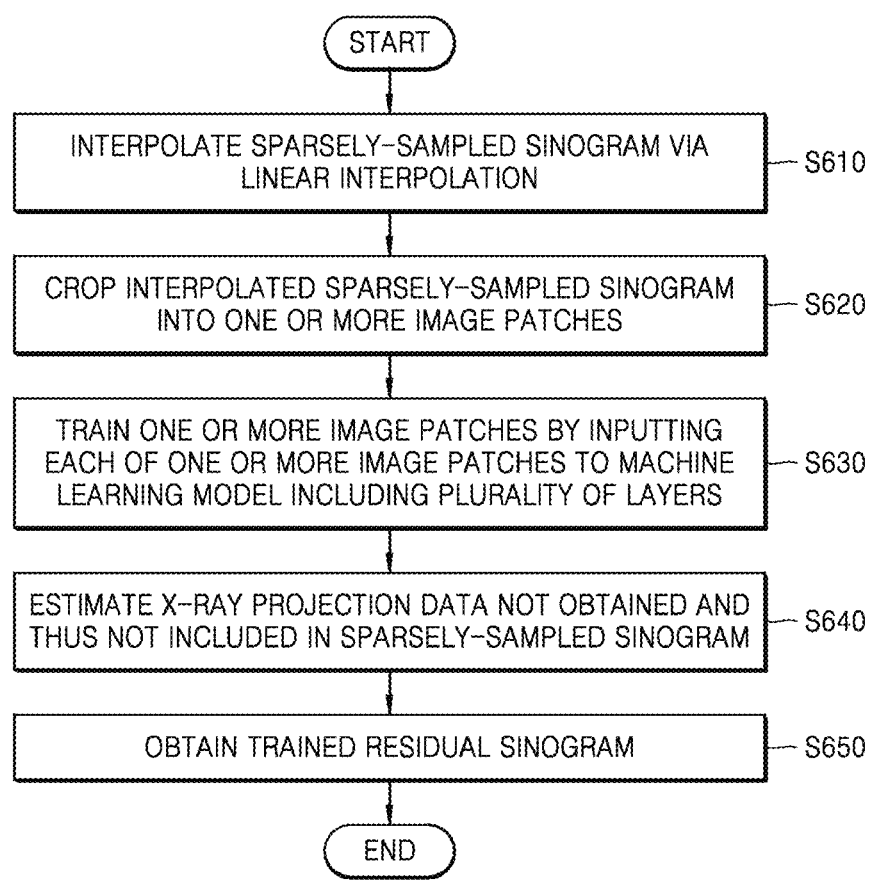
FIG. 6 is a flowchart of a method, performed by a CT imaging apparatus according to an embodiment, of interpolating an X-ray projection image by using a machine learning model.

FIG. 6 is a flowchart of a method in which a CT imaging apparatus according to an embodiment of the present disclosure interpolates an X-ray projection image by using a machine learning model. All operations illustrated in FIG. 6 may be equally performed not only in a CT imaging apparatus but also in a tomosynthesis imaging apparatus.

In operation S610, the CT imaging apparatus interpolates a sparsely-sampled sinogram via linear interpolation. The CT imaging apparatus may radiate X-rays at a plurality of angles while rotating the X-ray source 210 about the rotating axis at intervals of a preset angle, and may obtain the sparsely-sampled sinogram via X-rays detected at only a plurality of angles at which the X-rays have been radiated.

The CT imaging apparatus may interpolate X-ray projection data corresponding to angles at which the X-rays were not detected, instead of X-ray projection data obtained and accordingly included in the sparsely-sampled sinogram. The CT imaging apparatus may interpolate the X-ray projection data via linear interpolation, but embodiments are not limited thereto. According to an embodiment, the CT imaging apparatus may interpolate the sparsely-sampled sinogram via at least one of spline interpolation, polynomial interpolation, and already-well-known interpolation methods.

In operation S620, the CT imaging apparatus crops the interpolated sparsely-sampled sinogram into one or more image patches. According to an embodiment, the CT imaging apparatus may crop the interpolated sparsely-sampled sinogram into one or more image patches having a preset size. According to an embodiment, all of the plurality of image patches may have the same sizes. However, the CT imaging apparatus may input the sparsely-sampled sinogram to the machine learning model, without cropping the sparsely-sampled sinogram into image patches.

In operation S630, the CT imaging apparatus trains the one or more image patches by inputting each of the one or more image patches to a machine learning model including a plurality of layers. The applied machine learning model may include all methods and algorithms well known in the machine learning field, for example, at least one of an ANN, an SVM, and a deep learning network.

For example, the CT imaging apparatus may train the one or more image patches by applying a convolution layer using a filter having a preset number of channels and as many ReLU layers as the number of channels to each of the one or more image patches. A detailed description of operation S630 will refer to the description of FIG. 5.

In operation S640, the CT imaging apparatus estimates X-ray projection data not obtained and thus not included in the sparsely-sampled sinogram. For example, the CT imaging apparatus may extract a feature map of each of the image patches obtained in operation S620, by using a filter having a preset number of channels, for example, 64 channels each having a 3×3 size. The CT imaging apparatus may generate a feature map about all of the plurality of image patches by striding the filter, and may apply weights to the feature map by applying a plurality of convolution layers and a plurality of ReLU layers. X-ray projection data not obtained and thus not included in the sparsely-sampled sinogram may be estimated via a tiling process of sticking the one or more image patches having passed through the plurality of convolution layers and the plurality of ReLU layers together. The CT imaging apparatus may generate a densely-sampled sinogram including both the X-ray projection data included in the sparsely-sampled sinogram and the X-ray projection data estimated via training.

In operation S650, the CT imaging apparatus obtains a residual sinogram, which is a difference between the densely-sampled sinogram generated via training and the sparsely-sampled sinogram. Ideally, when training is perfectly performed, all pixel values of the residual sinogram may be 0.

Figure 7A:
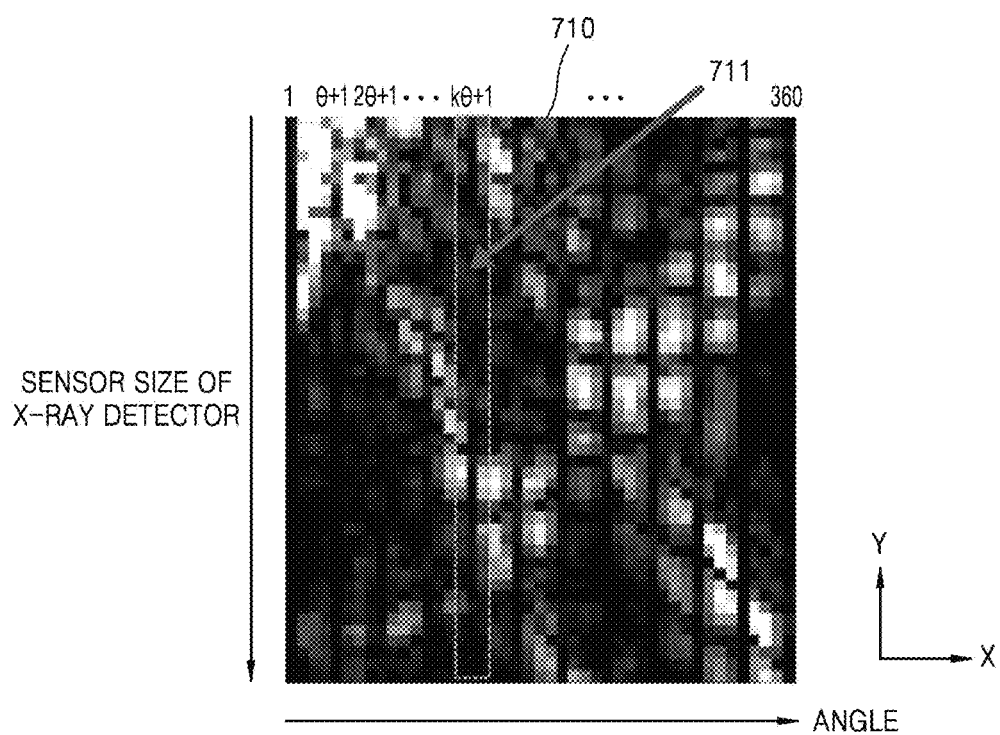
FIG. 7A is an image showing a residual sinogram trained via the machine learning model of FIGS. 5 and 6.

FIG. 7A is an image showing a residual sinogram trained by actually applying the machine learning model of FIGS. 5 and 6.

Referring to FIG. 7A, a trained residual sinogram 710 includes pieces of X-ray projection data trained in a first direction (X direction), in which pieces of X-ray projection data obtained by an X-ray source radiating X-rays onto an object at a plurality of angles while rotating are arranged, and in a second direction (Y direction), in which detector sensors are arranged. The second direction (Y direction) may mean a direction in which pieces of X-ray projection data obtained via X-rays detected by a sensor of an X-ray detector at specific angles are arranged.

The trained residual sinogram is a projection image representing a difference between a finally trained densely-sampled sinogram and an initially input sparsely-sampled sinogram. Thus, ideally, the values of pieces of X-ray projection data obtained at a plurality of angles need to be 0.

For example, in FIG. 7A, a base projection data line 711, which is a group of pieces of X-ray projection data respectively obtained at a plurality of angles arranged in the first direction (X direction), namely, 1°, θ+1, 2θ+1, ..., kθ+1, ..., and 360°, and arranged in the second direction (Y direction), may have a pixel value of 0. The second direction (Y direction) is a sensor size direction of the X-ray detector, and may mean a direction in which pieces of X-ray projection data obtained via X-rays detected by the sensor of the X-ray detector are arranged. The base projection data line 711 is defined as a group of pieces of X-ray projection data obtained via X-rays radiated onto an object at locations corresponding to a plurality of angles (for example, 1°, θ+1, 2θ+1, . . . , kθ+1, . . . , and 360°) while the X-ray source is rotating on the rotating frame, transmitted by the object, and detected by the X-ray detector.

The base projection data line 711 of FIG. 7A is not displayed in clear black, compared with the other X-ray projection data, because the training via the machine learning model described above with reference to FIGS. 5 and 6 is not for reconstructing medical images but is optimized for general images. In other words, when training is performed by applying a machine learning model to an actual sparsely-sampled sinogram, distortion may occur, and accordingly, some of the pieces of X-ray projection data included in the base projection data line 711 may have values that are not 0. Such a sinogram distortion may degrade precision of reconstructed image information when reconstructing a CT image from a sinogram later.

Figure 7B:
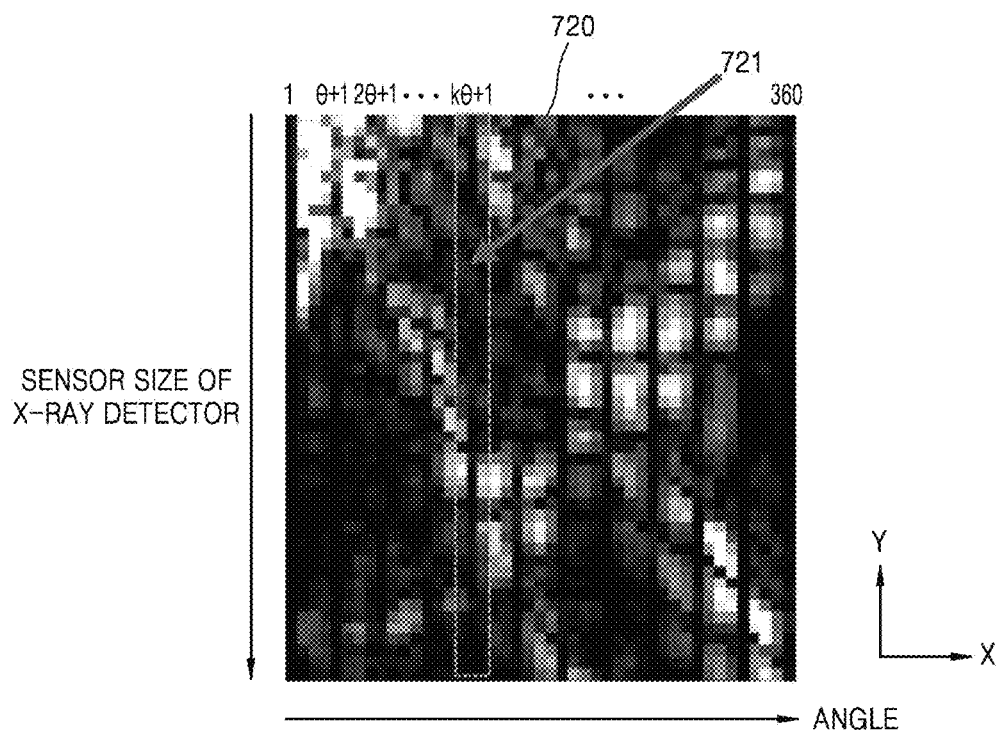
FIG. 7B is an image showing a desired residual sinogram of which base projection data has a value of 0.

FIG. 7B is an image showing an ideally-trained residual sinogram 720. Referring to FIG. 7B, in the case of the ideally-trained residual sinogram 720, a plurality of base projection data lines 721 are displayed more darkly than their surroundings and thus may be clearly recognized. This means that the pixel values of the base projection data lines 721 are 0.

Figure 8A:
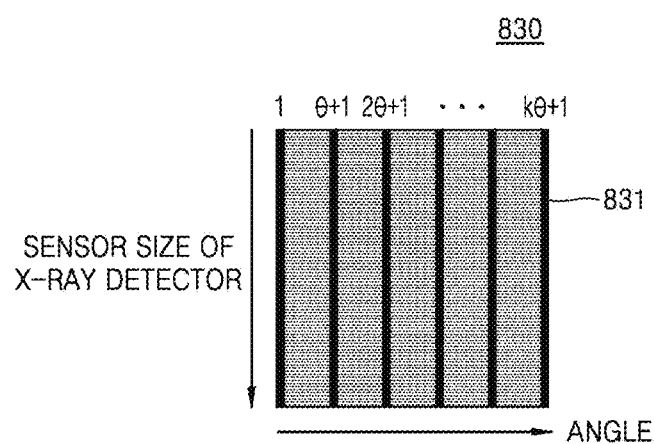
FIG. 8A is a conceptual view for explaining a base projection data preserving layer.

FIG. 8A is a conceptual view for explaining a base projection data preserving layer 830.

Referring to FIG. 8A, the base projection data preserving layer 830 may have the same size as that of a sparsely-sampled sinogram. In the base projection data preserving layer 830, base projection data lines 831 each extending in a sensor size direction of an X-ray detector at locations respectively corresponding to a plurality of preset angles, for example, 1°, θ+1, 2θ+1, . . . , kθ+1, . . . , and 360°, may have pixel values of 0. However, the pixel values of the base projection data lines 831 are not always 0. According to an embodiment, the base projection data lines 831 may have small pixel values that are not 0.

Figure 8B:
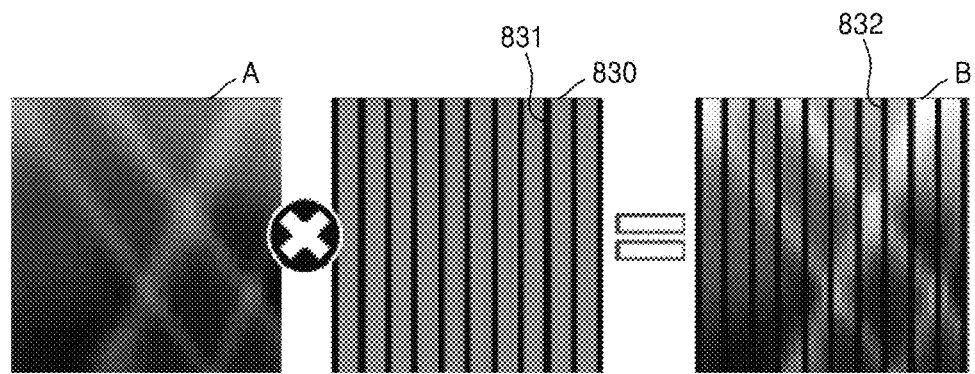
FIG. 8B is a conceptual view for explaining a method of applying a base projection data preserving layer to a residual sinogram.

FIG. 8B is a conceptual view for explaining a basic principle of generating a trained residual sinogram B by applying the base projection data preserving layer 830 to a residual sinogram A.

Referring to FIG. 8B, the CT imaging apparatus may apply the base projection data preserving layer 830 to the residual sinogram A. The residual sinogram A may be a projection image representing a difference between a densely-sampled sinogram trained via a machine learning model and a sparsely-sampled sinogram provided as an input. In the base projection data preserving layer 830, the base projection data lines 831 obtained at the preset angles have pixel values of 0. Thus, when the base projection data preserving layer 830 is trained via a multiplication with the residual sinogram A, the trained residual sinogram B also has base projection data lines 832 having pixel values of 0. In more detail, the pixel values of pieces of X-ray projection data arranged at locations corresponding to the base projection data lines 831 of the base projection data preserving layer 830 on the trained residual sinogram B are 0, and accordingly, the trained residual sinogram B may also include the base projection data lines 832.

Figure 8C:
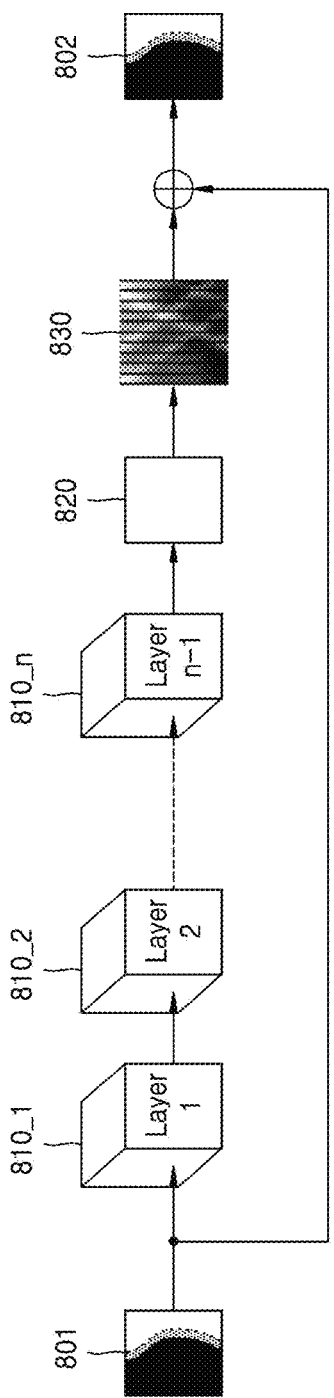
FIG. 8C is a conceptual view for explaining a method in which a CT imaging apparatus according to an embodiment applies a base projection data preserving layer to a residual sinogram trained via a machine learning model.

FIG. 8C is a conceptual view for explaining a method in which a CT imaging apparatus according to an embodiment of the present disclosure applies the base projection data preserving layer 830 to a residual sinogram 820 trained via a machine learning model. The machine learning model shown in FIG. 8C may be a model that is performed by an algorithm substantially the same as that for the machine learning model described above with reference to FIGS. 5 and 6. Accordingly, a repeated description of matters described above with reference to FIGS. 5 and 6 is omitted herein. The embodiment of applying the base projection data preserving layer 830 to the trained residual sinogram 820 using the machine learning model shown in FIG. 8C may be equally performed not only in a CT imaging apparatus but also in a tomosynthesis imaging apparatus.

Referring to FIG. 8C, the CT imaging apparatus may train a final densely-sampled sinogram 802 by applying a machine learning model including a plurality of layers 810_1 through 810_n to a sparsely-sampled sinogram 801. According to an embodiment, the CT imaging apparatus may crop the sparsely-sampled sinogram 801 into one or more image patches and may apply the machine learning model to each of the one or more image patches. In this case, a sinogram provided as an input to the machine learning model may be an image patch of the sparsely-sampled sinogram 801.

The CT imaging apparatus may train the sparsely-sampled sinogram 801 by using, for example, a deep learning network. In this case, the first through n-th layers 810_1 through 810_n may include a convolution layer and a ReLU layer. Because the machine learning model is configured to train the final densely-sampled sinogram 802 by sequentially applying the plurality of layers 810_1 through 810_n to the sparsely-sampled sinogram 801 and adding the initially-input sparsely-sampled sinogram 801 to the n-th layer 810_n again, the trained residual sinogram 820 may be obtained. The trained residual sinogram 820 may include projection image data corresponding to a difference between the densely-sampled sinogram 802 generated via training and the image patch of the sparsely-sampled sinogram 801 provided as an input to the machine learning model.

According to an embodiment, the CT imaging apparatus may additionally apply the base projection data preserving layer 830 to the trained residual sinogram 820. The base projection data preserving layer 830 may be a layer that processes the pixel value of projection data corresponding to the base projection data lines 831 corresponding to actually-obtained X-ray projection data lines on the sparsely-sampled sinogram 801 to be 0.

Accordingly, the pixel values of base projection data lines of the densely-sampled sinogram 802 trained by applying the base projection data preserving layer 830 may be equal to the pixel values of the actually obtained X-ray projection data lines of the sparsely-sampled sinogram 801 provided as an input.

The CT imaging apparatus using the machine learning model of FIG. 8C may reconstruct the pixel values of the base projection data lines of the densely-sampled sinogram 802 generated via training to be equal to the pixel values of pieces of X-ray projection data actually obtained by radiating X-rays, by applying the base projection data preserving layer 830 to the finally trained residual sinogram 820. Accordingly, the CT imaging apparatus according to the embodiment of FIG. 8C may reconstruct a CT image from a densely-sampled sinogram interpolated via the machine learning model, thereby increasing the image quality and precision of reconstruction.

Figure 8D:
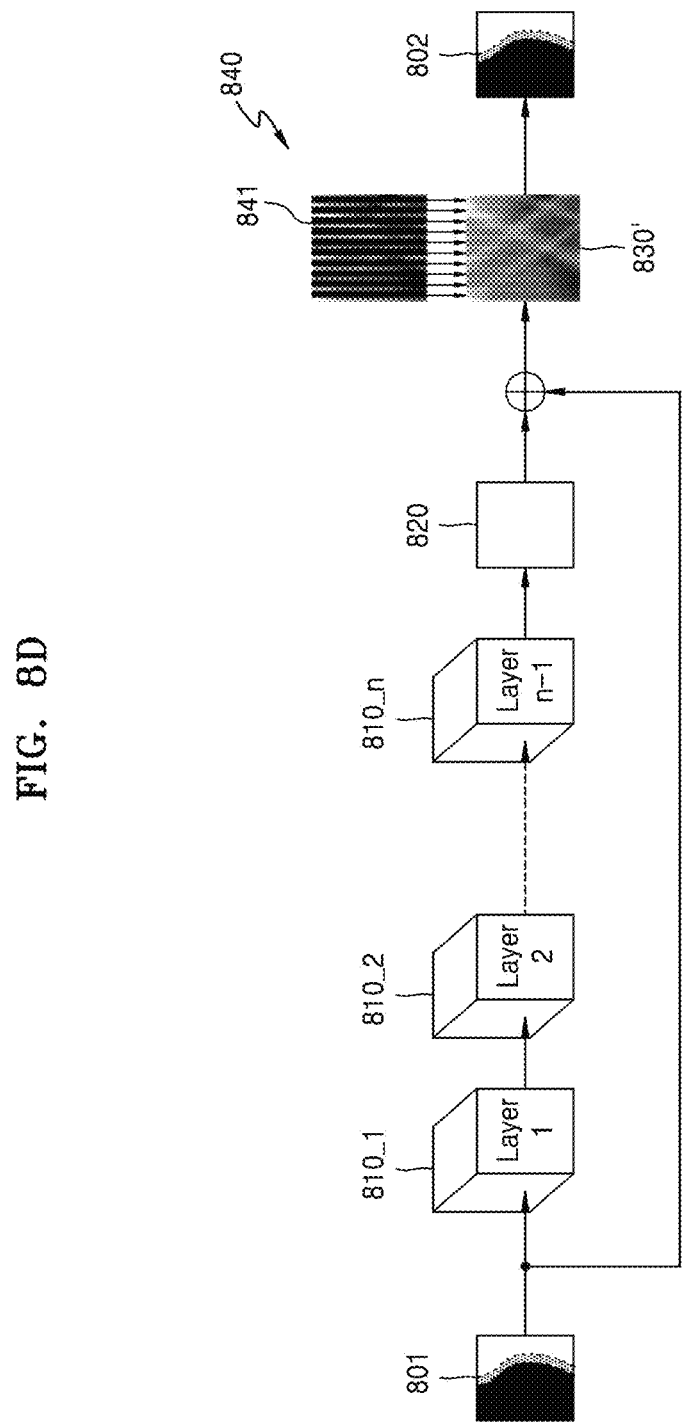
FIG. 8D is a conceptual view for explaining a method, performed by a CT imaging apparatus according to an embodiment, of applying a base projection data preserving layer to a sum of a residual sinogram trained via a machine learning model and an initially-input sparsely-sampled sinogram.

FIG. 8D is a conceptual view for explaining a method in which a CT imaging apparatus according to an embodiment of the present disclosure interpolates an X-ray projection data value of the densely-sampled sinogram 802 by estimating an X-ray projection data value of the initially input sparsely-sampled sinogram 801 via a machine learning model and then replacing the value of a base projection data line of the initially input sparsely-sampled sinogram 801. In the machine learning model of FIG. 8D, all well-known machine learning algorithms or methods including the plurality of layers 810_1 through 810_n may be performed. A repeated description of matters described above with reference to FIGS. 5 and 6 is omitted herein. The interpolation of the X-ray projection image by using the machine learning model shown in FIG. 8D may be equally performed not only in a CT imaging apparatus but also in a tomosynthesis imaging apparatus.

Referring to FIG. 8D, the CT imaging apparatus may train the final densely-sampled sinogram 802 by applying a machine learning model including the plurality of layers 810_1 through 810_n to the sparsely-sampled sinogram 801. The CT imaging apparatus may train the sparsely-sampled sinogram 801 by using, for example, a deep learning network. In this case, the first through n-th layers 810_1 through 810_n may include a convolution layer and a ReLU layer. Because the machine learning model is configured to train the final densely-sampled sinogram 802 by sequentially applying the plurality of layers 810_1 through 810_n to the sparsely-sampled sinogram 801 and adding the initially-input sparsely-sampled sinogram 801 to the n-th layer 810_n again, the trained residual sinogram 820 may be obtained.

According to the embodiment of FIG. 8D, the CT imaging apparatus may further include a component that adds the initially input sparsely-sampled sinogram 801 to the residual sinogram 820. After the residual sinogram 820 and the X-ray projection data of the sparsely-sampled sinogram 801 are summed, a base projection data preserving layer 830' may be applied. The CT imaging apparatus may apply, to the base projection data preserving layer 830', a replacement layer 840 that replaces the pixel values of base projection data lines, namely, one or more pieces of X-ray projection data obtained at a plurality of angular locations (referring to FIG. 8A, locations respectively corresponding to 1°, θ+1, 2θ+1, ..., kθ+1, ..., and 360°) by an X-ray source, with the values of pieces of X-ray projection data at angles corresponding to the plurality of angular locations included in the sparsely-sampled sinogram 801 initially input to the machine learning model. The replacement layer 840 may include base projection data lines 841 having the same pixel values as X-ray projection data values of the base projection data lines of the sparsely-sampled sinogram 801 initially input to the machine learning model. The replacement layer 840 may replace the pixel values of the base projection data lines of the base projection data preserving layer 830' with the pixel values of the base projection data lines of the initially input sparsely-sampled sinogram 801.

The value of the X-ray projection data of the final densely-sampled sinogram 802 may be estimated via the base projection data preserving layer 830' of which the values of the base projection data lines have been replaced via the replacement layer 840. In the machine learning model of FIG. 8D, due to the replacement layer 840 and the base projection data preserving layer 830', the pixel values of the base projection data lines of the final densely-sampled sinogram 802 may be equal to the pixel values of the X-ray projection data lines of the initially input sparsely-sampled sinogram 801. Accordingly, the CT imaging apparatus according to the embodiment of FIG. 8D may reconstruct a CT image from a densely-sampled sinogram interpolated via the machine learning model, thus the CT imaging apparatus may cause an effect of improving image quality and precision of the reconstructed image.

Figure 9A:
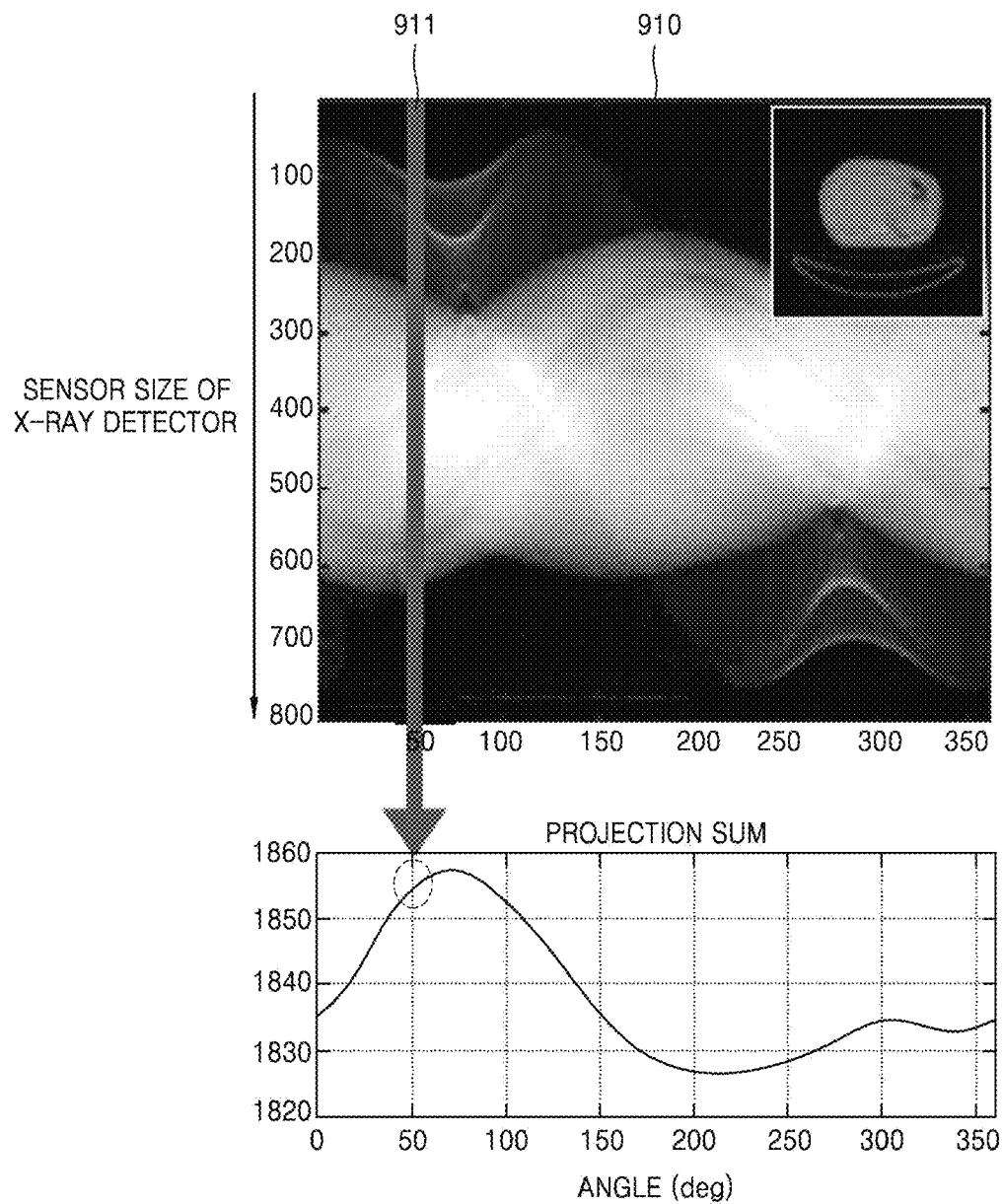
FIG. 9A is a view for explaining a tendency of a projection sum, which is a sum of a sinogram in a sensor direction of an X-ray detector.

FIG. 9A is a view for explaining tendency of a projection sum, which is a sum of a sinogram in a sensor direction of an X-ray detector.

Referring to FIG. 9A, a projection sum value, which is a sum of the pixel values of X-ray projection data of a sinogram 910 in a size direction of an X-ray detector sensor at a specific angle is not greatly different from a projection sum value at an angle adjacent to the specific angle and has constant tendency. For example, when the value of a first projection sum 911, which is a sum of X-ray projection data obtained at 50° in the size direction of the X-ray detector sensor, is 1854, a projection sum obtained by summing X-ray projection data obtained at 51° in the size direction of the X-ray detector sensor may have a value of 1855 or 1854.xx.

In other words, projection sums obtained at neighboring angles are not greatly different from each other or are slightly different from each other. However, as for a densely-sampled sinogram trained via a machine learning model, projection sums obtained at neighboring angles may be relatively greatly different from each other, because, when the machine learning model of FIGS. 5 and 6 is applied, a sparsely-sampled sinogram is cropped into the plurality of image patches 501. A tiling process is performed to stick image patches of the final densely-sampled sinogram 502 trained via the cropping into the plurality of image patches 501 together. In this case, distortion may occur on a boundary between the stuck patches. This will now be described in detail with reference to FIG. 9B.

Figure 9B:
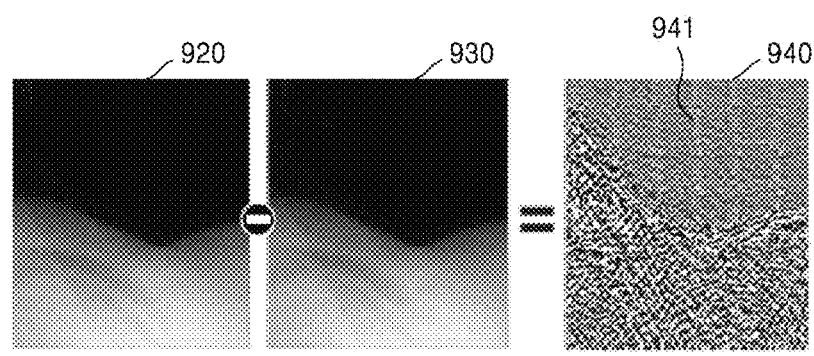
FIG. 9B is a view for explaining a tiling artifact of a sinogram interpolated via a machine learning model.

FIG. 9B is a view for explaining a tiling artifact of a sinogram interpolated via a machine learning model.

Referring to FIG. 9B, when a difference between a full-sampled sinogram 920 and a densely-sampled sinogram 930 trained via a machine learning model is calculated, a tiling artifact may occur. In other words, referring to a difference image 940 obtained by subtracting the densely-sampled sinogram 930 trained via the machine learning model from the full-sampled sinogram 920, the difference image 940 may include a tiling artifact 941 vaguely expressed in a lattice pattern. The tiling artifact 941 occurs because, to simplify image processing and calculations during training via a machine learning model, a sparsely-sampled sinogram is cropped into a plurality of image patches, each of the plurality of image patches is trained, and then image patches of a final trained densely-sampled sinogram are stuck together.

Training general images is not affected by a tiling artifact because the tiling artifact has a small value, whereas medical images needed to be reconstructed to an accurate value may be affected by a tiling artifact. Occurrence of the tiling artifact 941 may be prevented by overlappingly extracting a plurality of image patches and overlapping training results with each other. However, in this case, calculation and training time periods increase in proportion to an extent of an overlapped area. Accordingly, to prevent occurrence of the tiling artifact 941 without overlapping the plurality of image patches, the respective sizes of the plurality of image patches need to be increased. A detailed method of increasing the sizes of image patches will be described in detail with reference to FIGS. 10A through 10C.

Figure 10A:
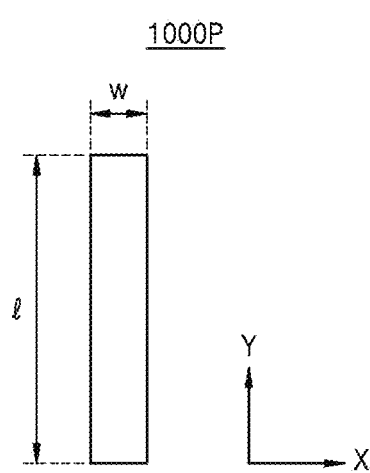
FIG. 10A illustrates the size of an image patch that a CT imaging apparatus according to an embodiment inputs to a machine learning model.

FIG. 10A is a diagram for explaining the size of an image patch that a CT imaging apparatus according to an embodiment of the present disclosure inputs to a machine learning model.

Referring to FIG. 10A, the CT imaging apparatus may crop a sparsely-sampled sinogram into a plurality of image patches each having a preset size in order to reduce the amounts of calculation and training, before inputting the sparsely-sampled sinogram to the machine learning model and training the sparsely-sampled sinogram. According to the embodiment of FIG. 10A, the CT imaging apparatus may crop the sparsely-sampled sinogram into image patches 1000P each having a size l equal to a sensor size of an X-ray detector in a first direction (X direction) and a preset width w in a second direction (Y direction) perpendicular to the first direction (X direction). The first direction (X direction) may be a direction in which pieces of X-ray projection data obtained at the same angle within the sparsely-sampled sinogram are arranged, and the second direction (Y direction) may be a direction in which pieces of X-ray projection data obtained at a plurality of angles where an X-ray radiator rotates around an object are arranged.

For example, each image patch 1000p may be 800×41. This may mean that the width w of the image patch 1000P in the first direction (X direction) has 41 pixels and the size l, i.e., a length l, of the image patch 1000P in the second direction (Y direction), namely, the size of the X-ray detector sensor, has 800 pixels. However, the value of the size of the image patch 1000P is merely an example. According to embodiments, the size of the image patch 1000P is not limited thereto.

The CT imaging apparatus may crop the length l of the image patch 1000P in the second direction (Y direction) to be equal to the sensor size of the X-ray detector, and stick individually-trained image patches 1000P together, thereby removing a tiling artifact in a horizontal direction, namely, the first direction (X direction). Moreover, compared with overlapping and training image patches, calculation and training time periods may be reduced by 60% or greater. A method of cropping the length l of the image patch 1000P in the second direction (Y direction) to the sensor size of the X-ray detector to train the cropped image patch 1000P via the machine learning model will now be described in detail with reference to FIG. 10B.

Figure 10B:
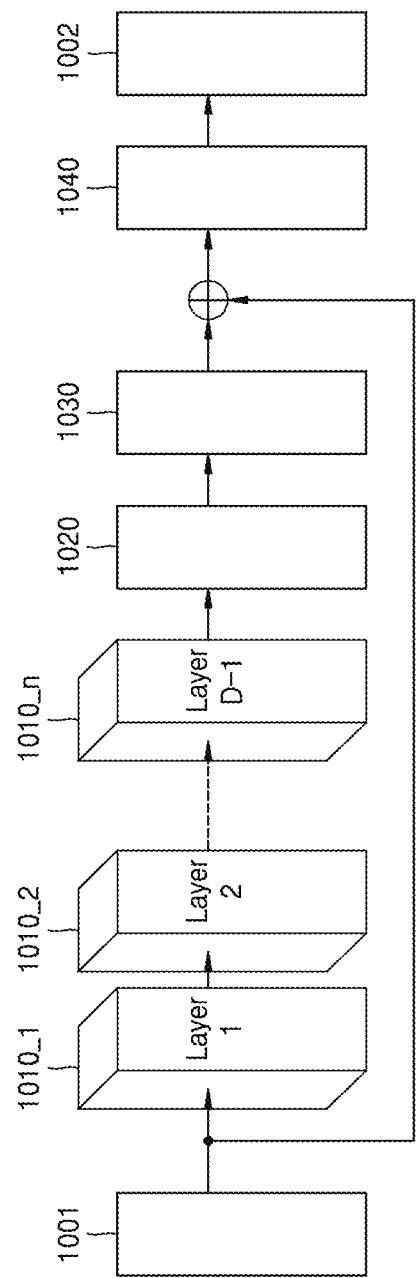
FIG. 10B is a schematic diagram for explaining a method, performed by a CT imaging apparatus according to an embodiment, of applying a projection sum preserving layer to a densely-sampled sinogram interpolated via a machine learning model.

FIG. 10B is a schematic diagram for explaining a method in which a CT imaging apparatus according to an embodiment of the present disclosure applies a projection sum preserving layer 1040 to a densely-sampled sinogram 1002 interpolated via a machine learning model.

The machine learning model shown in FIG. 10B may be a machine learning network that is substantially the same as the machine learning model described above with reference to FIGS. 5 and 6. Accordingly, a repeated description of matters described above with reference to FIGS. 5 and 6 is omitted herein. The method of applying the projection sum preserving layer 1040 during interpolation of an X-ray projection image by using the machine learning model shown in FIG. 10B may be equally performed not only in a CT imaging apparatus but also in a tomosynthesis imaging apparatus.

Referring to FIG. 10B, the CT imaging apparatus may crop a sparsely-sampled sinogram into image patches 1001 each having a preset size. Similar to the image patch 1000P of FIG. 10A, each image patch 1001 may have the same size as the sensor size of an X-ray detector in a vertical direction, namely, in a direction in which pieces of X-ray projection data obtained via X-rays detected by a sensor of the X-ray detector are arranged. The CT imaging apparatus may train the image patch 1001 by applying the image patch 1001 to a machine learning model including a plurality of layers 1010_1 through 1010_n. For example, the CT imaging apparatus may generate a feature map by applying the image patch 1001 to the plurality of layers 1010_1 through 1010_n including a plurality of convolution layers using a filter having a preset number of channels and a plurality of ReLU layers.

The CT imaging apparatus may obtain the densely-sampled sinogram 1002 by adding the image patch 1001 of the sparsely-sampled sinogram initially provided as an input to a residual sinogram 1020 calculated by passing through the n-th layer 1010_n. Because the machine learning model of FIG. 10B includes a component that summing the image patch 1001 initially provided as an input, the residual sinogram 1020 may be generated. The residual sinogram 1020 is the same as the residual sinogram 520 described above with reference to FIG. 5, and thus a detailed description thereof will be omitted.

The CT imaging apparatus may additionally apply a base projection data preserving layer 1030 to the trained residual sinogram 1020. The base projection data preserving layer 1030 may be a layer that preserves a pixel value of a base projection data line of the residual sinogram 1020 trained via the plurality of layers 1010_1 through 1010_n to be equal to a pixel value of projection data corresponding to a base projection data line of the initially-input image patch 1001 of the sparsely-sampled sinogram. According to an embodiment, a pixel value corresponding to the base projection data line from among pixel values of the base projection data preserving layer 1030 may be 0.

The CT imaging apparatus may apply the projection sum preserving layer 1040, which equalizes a sum of pieces of X-ray projection data obtained at the same angle from among pieces of X-ray projection data included in the densely-sampled sinogram 1002 finally generated via the machine learning model to a sum of pieces of X-ray projection data obtained at corresponding angular locations on the image patch 1001 of the sparsely-sampled sinogram. The projection sum preserving layer 1040 may interpolate the value of trained X-ray projection data, based on a projection sum 1041 (see FIG. 10C) obtained by summing pieces of X-ray projection data obtained at a first angle θ1 (see FIG. 10C) in a sensor size direction of an X-ray detector. This will be described in greater detail later with reference to FIG. 10C.

Figure 10C:
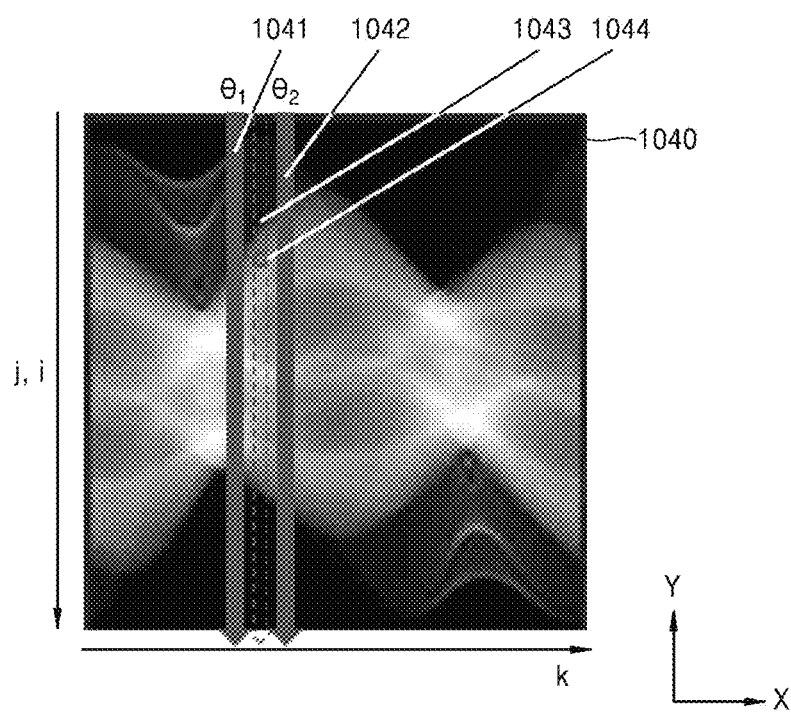
FIG. 10C is an image for explaining a method, performed by a projection sum preserving layer, of interpolating the value of each X-ray projection data included in a densely-sampled sinogram.

FIG. 10C is an image for explaining a method in which the projection sum preserving layer 1040 interpolates the value of each X-ray projection data included in the densely-sampled sinogram 1002.

Referring to FIGS. 10B and 10C, the CT imaging apparatus may apply the projection sum preserving layer 1040 to the densely-sampled sinogram 1002. Pieces of X-ray projection data arranged in the second direction (Y direction) at the first angle θ1 and a second angle θ2 are obtained by an X-ray detector detecting X-rays that an X-ray source radiates onto an object at a plurality of angles while rotating on a rotating frame, and accordingly, are defined as base projection data. The CT imaging apparatus may interpolate the pixel values of pieces of trained X-ray projection data in a densely-sampled sinogram arranged between pieces of first base projection data at the first angle θ1 and pieces of second base projection data at the second angle θ2, based on the sum 1041 of the pieces of first base projection data and a sum 1042 of the pieces of second base projection data.

According to an embodiment, a vector of the X-ray projection data included in the projection sum preserving layer 1040 may be defined using Equation 1:

$$\text{Projection vector } x_{(k)} = [x_{(k),1}, \ldots, x_{(k),N}],$$

A forward propagation function $f(x(k),i)$ of the projection sum preserving layer 1040 is defined using Equation 2:

$$f(x_{(k),i}) = \frac{\sum_j x_{(k),j}^{(target)}}{\sum_j x_{(k),j}} \cdot x_{(k),i} = \frac{C \cdot x_{(k),i}}{\sum_j x_{(k),j)}},$$

where N indicates the number of pixels of an X-ray detector and K indicates a width of an image patch. A reference character C in Equation 2 is defined using Equation 3:

$$C \equiv \sum_j x_{(k),j}^{(target)}, i,j=0,1, \ldots, N \text{ and}, k=1,2, \ldots, K$$

An error back-propagation function $\partial f(x_{(k),j})/\partial x_{(k),i}$ of the projection sum preserving layer 1040 is defined using Equation 4:

$$\frac{\partial f(x_{(k),i})}{\partial x_{(k),i}} = \frac{\partial}{\partial x_{(k),i}}\left(\frac{Cx_{(k),i}}{\sum x_{(k),j}}\right) = \frac{C}{\sum_j x_{(k),j}} + \frac{-Cx_{(k),i}}{\left(\sum_j x_{(k),j}\right)^2} = \frac{C}{\sum_j x_{(k),j}}\left(1 - \frac{x_{(k),i}}{\sum_j x_{(k),j}}\right)$$

In Equations 2 through 4, C indicates a constant. The constant C may be obtained from base projection data adjacent to the pieces of trained X-ray projection data via interpolation using linear interpolation. In FIG. 10C, a pixel value (x(k), i) of X-ray projection data 1044 may be calculated via a ratio between a sum $\Sigma_j x(k),j$ 1043 of pieces of densely-sampled X-ray projection data and the sum 1041 (C) of the pieces of first base projection data adjacent to the pieces of densely-sampled X-ray projection data. The calculation is performed using Equation 2, and an error may be calculated using Equation 4. According to an embodiment, the pixel value (x(k), i) of the X-ray projection data 1044 may also be calculated via a ratio between the sum $\Sigma_j x(k),j$ 1043 of the pieces of densely-sampled X-ray projection data and the sum 1042 (C) of the pieces of second base projection data adjacent to the pieces of densely-sampled X-ray projection data.

The pixel value of the trained X-ray projection data is interpolated via the projection sum preserving layer 1040 of FIG. 10C one more time, thereby increasing the accuracy of the densely-sampled sinogram 1002.

Figure 11:
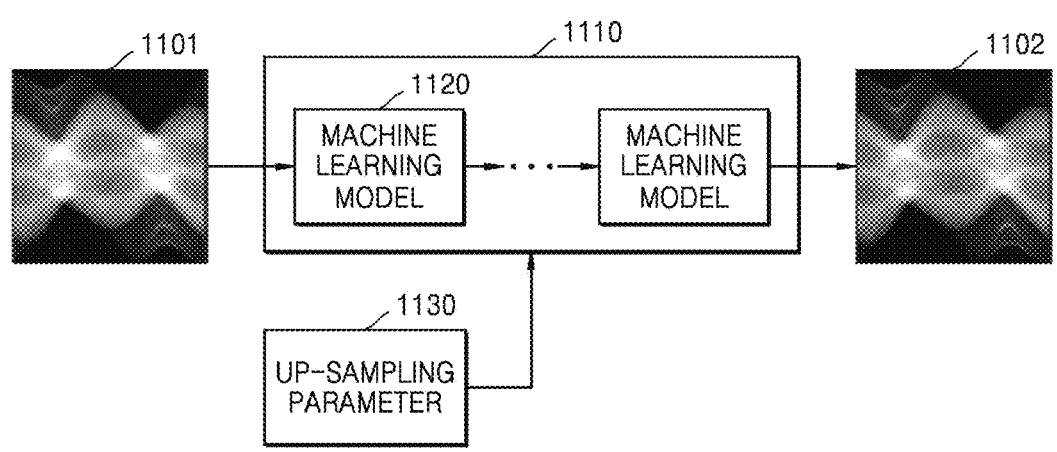
FIG. 11 is a conceptual view for explaining a method, performed by a CT imaging apparatus according to an embodiment, of improving the image quality of a trained sinogram by connecting machine learning models in a cascade manner.

FIG. 11 is a conceptual view for explaining a method in which a CT imaging apparatus according to an embodiment of the present disclosure improves the image quality of a trained sinogram by connecting machine learning models in a cascade manner. The embodiment of connecting the machine learning models in a cascade manner illustrated in FIG. 11 may be equally performed not only in a CT imaging apparatus but also in a tomosynthesis imaging apparatus.

Referring to FIG. 11, the CT imaging apparatus may train a sparsely-sampled sinogram 1101 by applying a model parameter to the sparsely-sampled sinogram 1101 via an interpolation system 1110 including a plurality of machine learning models 1120 in order to increase the number of pieces of trained X-ray projection data. The interpolation system 1110 may be configured by connecting, in a cascade manner, the plurality of machine learning models 1120 including one of the machine learning models of FIGS. 5, 8C, 8D, and 10B or a combination thereof.

The interpolation system 1110 may perform application of the plurality of machine learning models 1120 in stages in order to the number of pieces of trained X-ray projection data in the sparsely-sampled sinogram 1101. The interpolation system 1110 may set an up-sampling parameter 1130 in order to improve the resolution and image quality of a finally-trained densely-sampled sinogram 1102. As the size of the up-sampling parameter 1130 increases and the number of machine learning models 1120 connected to each other in a cascade manner increases, the image quality of the trained densely-sampled sinogram 1102 improves. For example, when the up-sampling parameter 1130 is doubled, every time one machine learning model 1120 is applied, resolution of the trained densely-sampled sinogram 1102 may increase to two times, four times, eight times, . . . , and $2n$. However, as a setting value of the up-sampling parameter 1130 increases, the time taken for training may increase.

When the sparsely-sampled sinogram 1101 is trained via the interpolation system 1110 of FIG. 11, the base projection data preserving layer 830 of FIG. 8C or 1030 of FIG. 10B may be equally applied to the plurality of machine learning models 1120.

Figure 12:
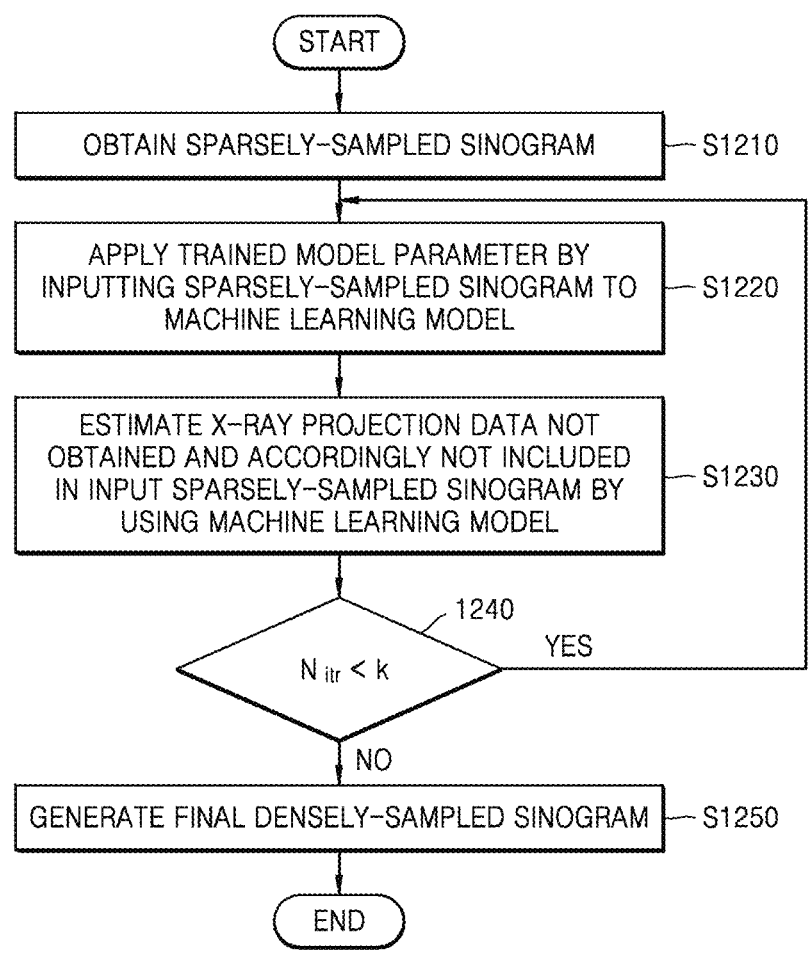
FIG. 12 is a flowchart of a method, performed by a CT imaging apparatus according to an embodiment, of improving the image quality of a sinogram trained via a machine learning model.

FIG. 12 is a flowchart of a method in which a CT imaging apparatus according to an embodiment of the present disclosure improves the image quality of a sinogram trained via a machine learning model. All operations illustrated in FIG. 12 may be performed equally not only in a CT imaging apparatus but also in a tomosynthesis imaging apparatus.

In operation S1210, the CT imaging apparatus obtains a sparsely-sampled sinogram. The CT imaging apparatus may radiate X-rays at a plurality of angles while rotating an X-ray source about an axis using an object as its center at intervals of a preset angle, and may detect the radiated X-rays via an X-ray detector, thereby obtaining the sparsely-sampled sinogram.

In operation S1220, the CT imaging apparatus applies a trained model parameter by inputting the sparsely-sampled sinogram to a machine learning model. According to an embodiment, the CT imaging apparatus may obtain a trained model parameter via training using a machine learning model that uses at least one sub-sampled sinogram as an input and uses a full-sampled sinogram for learning as a ground truth. The CT imaging apparatus may apply the trained model parameter by inputting the sparsely-sampled sinogram obtained in operation S1210 to the machine learning model. For example, the CT imaging apparatus may crop the sparsely-sampled sinogram into a plurality of image patches, and input each of the plurality of image patches to a machine learning model including a CNN using a filter having a preset number of channels and an ReLU, to thereby train the sparsely-sampled sinogram.

In operation S1230, the CT imaging apparatus estimates X-ray projection data not obtained and accordingly not included in the input sparsely-sampled sinogram by using the machine learning model. According to an embodiment, the CT imaging apparatus may estimate the value of X-ray projection data excluding X-ray projection data actually obtained and included in the sparsely-sampled sinogram, by applying a model parameter via the machine learning model. By interpolating X-ray projection data with the estimated value, the CT imaging apparatus may generate a densely-sampled sinogram including more pieces of X-ray projection data than the sparsely-sampled sinogram and having an improved image quality. According to an embodiment, the CT imaging apparatus may apply an up-sampling parameter to the machine learning model. For example, when the up-sampling parameter is doubled, the image quality of the sparsely-sampled sinogram may be doubled by passing through one machine learning model.

In operation S1240, the CT imaging apparatus connects machine learning models to each other in a cascade manner and determines whether the number $N_{itr}$ of iterations of applying a machine learning model is less than a preset number k. Referring to FIG. 11, the CT imaging apparatus may configure the interpolation system 1110 by connecting the plurality of machine learning models 1120 to each other in a cascade manner. The number of machine learning models 1120 connected to each other within the interpolation system 1110 may be equal to the number $N_{itr}$ in operation S1240. In other words, when the number $N_{itr}$ of iteration machine learning models consecutively applied is less than the preset number k, the CT imaging apparatus may perform training according to a method of applying once a model parameter to the sparsely-sampled sinogram input to a machine learning model to make the input sparsely-sampled sinogram pass through the machine learning model and inputting an output sinogram (densely-sampled sinogram) to a next machine learning model to apply the model parameter again.

When it is determined in operation S1240 that the number $N_{itr}$ of iteration is equal to or greater than the preset number k, the CT imaging apparatus generates a final densely-sampled sinogram, in operation S1250.

The above-described embodiments of the present disclosure may be embodied in a tomosynthesis imaging apparatus.

The above-described embodiments of the present disclosure may be embodied in form of a computer-readable recording medium for storing computer executable command languages and data. The command languages may be stored in form of program codes and, when executed by a processor, may perform a certain operation by generating a certain program module. Furthermore, when being executed by the processor, the instructions may perform specific operations according to the embodiments.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims. The exemplary embodiments should be considered in descriptive sense only and not for purposes of limitation.

What is claimed is:

1. A method comprising:
    radiating X-rays onto an object at a plurality of preset angular locations via an X-ray source, and obtaining a sparsely-sampled sinogram including X-ray projection data obtained via the X-rays that passed through the object;
    applying a trained model parameter to the sparsely-sampled sinogram by using a machine learning model, to thereby generate trained image data, wherein the trained model parameter is obtained via the machine learning model that uses a sub-sampled sinogram for learning as an input and uses a full-sampled sinogram for learning as a ground truth;
    estimating, from the sparsely-sampled sinogram, X-ray projection data with respect to the object that is not included in the sparsely-sampled sinogram; and
    generating a densely-sampled sinogram using the trained image data and the estimated X-ray projection data.

2. The method of claim 1, further comprising:
    interpolating the sparsely-sampled sinogram via linear interpolation before applying the trained model parameter to the sparsely-sampled sinogram.

3. The method of claim 1, wherein
    the machine learning model includes a plurality of layers, and
    the applying of the trained model parameter comprises:
        cropping the sparsely-sampled sinogram into at least one image patch, and
        applying the trained model parameter to the at least one image patch using the machine learning model including the plurality of layers.

4. The method of claim 3, further comprising:
    obtaining a residual sinogram; and
    maintaining a value of trained X-ray projection data at the plurality of preset angular locations included in the residual sinogram to be equal to a value of X-ray projection data at angles corresponding to the plurality of preset angular locations included in the sparsely-sampled sinogram.

5. The method of claim 4, wherein the residual sinogram is a sinogram indicating a difference between the densely-sampled sinogram and the sparsely-sampled sinogram.

6. The method of claim 5, wherein
    the maintaining comprises:
        applying, to the residual sinogram, a base projection data preserving layer that maintains the value of the trained X-ray projection data at the plurality of preset angular locations included in the residual sinogram to be equal to the value of the X-ray projection data at the angles corresponding to the plurality of preset angular locations included in the sparsely-sampled sinogram, and
        adding the sparsely-sampled sinogram to the residual sinogram to which the base projection data preserving layer has been applied, and
    the base projection data preserving layer processes a pixel value of at least one piece of X-ray projection data at the plurality of preset angular locations to be 0.

7. The method of claim 6, wherein
    the maintaining comprises applying a base projection data maintaining layer that replaces a pixel value of at least one piece of X-ray projection data obtained at the plurality of angular locations with the value of the X-ray projection data obtained at the angles corresponding to the plurality of angular locations included in the sparsely-sampled sinogram initially provided as an input, and
    the applying of the base projection data preserving layer is performed after the adding of the sparsely-sampled sinogram initially provided as an input to the residual sinogram.

8. The method of claim 1, further comprising:
    cropping the sparsely-sampled sinogram into one or more image patches each having a length equal to a sensor size of an X-ray detector in a first direction and a preset width in a second direction perpendicular to the first direction,
    wherein the applying of the trained model parameter comprises applying the trained model parameter to the one or more image patches by using the machine learning model.

9. The method of claim 1, further comprising:
    equalizing a sum of pieces of X-ray projection data at a same angular location from among one or more pieces of X-ray projection data included in the densely-sampled sinogram to a sum of pieces of X-ray projection data at an angle corresponding to a same angular location included in the sparsely-sampled sinogram.

10. The method of claim 9, wherein the equalizing comprises:
   interpolating values of trained pieces of X-ray projection data, based on a sum of pieces of X-ray projection data at a first angular location included in the densely-sampled sinogram and a sum of pieces of X-ray projection data at a second angular location that is adjacent to the first angular location included in the densely-sampled sinogram.

11. The method of claim 1, further comprising:
   applying the trained model parameter to the densely-sampled sinogram by using the machine learning model, to thereby train the densely-sampled sinogram; and
   applying the trained model parameter to the trained densely-sampled sinogram using the machine learning model.

12. An apparatus comprising:
   an X-ray source configured to radiate X-rays to an object at a plurality of preset angular locations;
   an X-ray detector configured to detect the X-rays radiated by the X-ray source and passed through the object; and
   at least one processor configured to cause the following to be performed:
      applying, using a machine learning model, a trained model parameter to a sparsely-sampled sinogram obtained via the X-rays detected by the X-ray detector, to thereby generate trained image data, wherein the trained model parameter is obtained via the machine learning model that uses a sub-sampled sinogram for learning as an input and uses a full-sampled sinogram for learning as a ground truth,
      estimating, from the sparsely-sampled sinogram, X-ray projection data with respect to the object that is not included in the sparsely-sampled sinogram, and
      generating a densely-sampled sinogram using the trained image data and the estimated X-ray projection data.

13. The apparatus of claim 12, wherein the at least one processor is further configured to cause the following to be performed:
   interpolating the sparsely-sampled sinogram via linear interpolation before applying the trained model parameter to the sparsely-sampled sinogram.

14. The apparatus of claim 12, wherein
   the at least one processor is further configured to cause the following to be performed:
      cropping the sparsely-sampled sinogram into at least one image patch, and
      the applying the trained model parameter comprises applying the trained model parameter to the at least one image patch using the machine learning model.

15. The apparatus of claim 14, wherein the at least one processor is further configured to cause the following to be performed:
   obtaining a residual sinogram; and
   maintaining a value of trained X-ray projection data at the plurality of preset angular locations included in the residual sinogram to be equal to a value of X-ray projection data at angles corresponding to the plurality of preset angular locations included in the sparsely-sampled sinogram.

16. The apparatus of claim 15, wherein the residual sinogram is a sinogram indicating a difference between the densely-sampled sinogram and the sparsely-sampled sinogram.

17. The apparatus of claim 16, wherein
   the maintaining comprises:
      applying, to the residual sinogram, a base projection data preserving layer that maintains the value of the trained X-ray projection data at the plurality of preset angular locations included in the residual sinogram to be equal to the value of the X-ray projection data at the angles corresponding to the plurality of preset angular locations included in the sparsely-sampled sinogram, and
      adding the sparsely-sampled sinogram to the residual sinogram to which the base projection data preserving layer has been applied, and
   the base projection data preserving layer processes a pixel value of at least one piece of X-ray projection data at the plurality of preset angular locations to be 0.

18. The apparatus of claim 16, wherein
   the at least one processor is further configured to apply a base projection data preserving layer that replaces a pixel value of at least one piece of X-ray projection data obtained at the plurality of angular locations with the value of the X-ray projection data obtained at the angles corresponding to the plurality of angular locations included in the sparsely-sampled sinogram initially provided as an input, and
   the base projection data preserving layer is applied after the sparsely-sampled sinogram initially provided as an input is added to the residual sinogram.

19. The apparatus of claim 12, wherein
   the at least one processor is further configured to cause the following to be performed:
      cropping the sparsely-sampled sinogram into one or more image patches each having a length equal to a sensor size of an X-ray detector in a first direction and a preset width in a second direction perpendicular to the first direction, and
   the applying the trained model parameter comprises applying the trained model parameter to the one or more image patches by using the machine learning model.

20. The apparatus of claim 12, wherein the at least one processor is further configured to cause the following to be performed:
   equalizing a sum of pieces of X-ray projection data at a same angular location from among one or more pieces of X-ray projection data included in the densely-sampled sinogram to a sum of pieces of X-ray projection data at an angular location corresponding to a same angular location included in the sparsely-sampled sinogram.

21. The apparatus of claim 20, wherein the at least one processor is further configured to cause the following to be performed:
   interpolating values of trained pieces of X-ray projection data, based on a sum of pieces of X-ray projection data at a first angular location included in the densely-sampled sinogram and a sum of pieces of X-ray projection data at a second angular location that is adjacent to the first a angular location included in the densely-sampled sinogram.

22. The apparatus of claim 12, wherein the at least one processor is further configured to cause the following to be performed:

applying the trained model parameter to the densely-sampled sinogram by using the machine learning model, to thereby train the densely-sampled sinogram, and applying the trained model parameter to the trained densely-sampled sinogram using the machine learning model.

23. A computer program product comprising a non-transitory computer-readable storage medium having a computer-readable program stored therein, wherein the computer-readable program, when executed on a computing device, causes the computing device to:

obtain a sparsely-sampled sinogram including X-ray projection data obtained via X-rays radiated onto an object at a plurality of preset angular locations via an X-ray source and detected at the plurality of preset angular locations;

apply a trained model parameter to the sparsely-sampled sinogram by using a machine learning model, to thereby generate trained image data, wherein the trained model parameter is obtained via the machine learning model that uses a sub-sampled sinogram for learning as an input and uses a full-sampled sinogram for learning as a ground truth;

estimate, from the sparsely-sampled sinogram, X-ray projection data with respect to the object that is not included in the sparsely-sampled sinogram; and generate a densely-sampled sinogram using the trained image data and the estimated X ray projection data.

* * * * *